United States Patent
Demmer et al.

(10) Patent No.: US 10,286,214 B2
(45) Date of Patent: May 14, 2019

(54) ATRIAL TRACKING IN AN INTRACARDIAC VENTRICULAR PACEMAKER

(71) Applicant: Medtronic, Inc., Minneapolis, MN (US)

(72) Inventors: Wade M Demmer, Coon Rapids, MN (US); Yong K Cho, Excelsior, MN (US); Mark K Erickson, Brooklyn Park, MN (US); Michael F Hess, Minneapolis, MN (US); Todd J Sheldon, North Oaks, MN (US); Vincent E Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 250 days.

(21) Appl. No.: 15/342,699

(22) Filed: Nov. 3, 2016

(65) Prior Publication Data
US 2018/0117337 A1  May 3, 2018

(51) Int. Cl.
*A61N 1/365* (2006.01)
*A61N 1/05* (2006.01)
*A61N 1/368* (2006.01)
*A61N 1/375* (2006.01)
*A61N 1/372* (2006.01)

(52) U.S. Cl.
CPC ....... *A61N 1/36542* (2013.01); *A61N 1/0573* (2013.01); *A61N 1/3682* (2013.01); *A61N 1/3684* (2013.01); *A61N 1/36578* (2013.01); *A61N 1/3756* (2013.01); *A61N 1/37205* (2013.01)

(58) Field of Classification Search
CPC .............. A61N 1/365; A61N 1/36514; A61N 1/36542; A61N 1/36578; A61N 1/3682; A61N 1/37; A61N 1/3702; A61N 1/37205; A61N 1/3756
See application file for complete search history.

(56) References Cited

U.S. PATENT DOCUMENTS

| | | |
|---|---|---|
| D879,280 | 2/1908 | Loberg |
| 4,485,813 A | 12/1984 | Anderson et al. |
| 5,052,388 A | 10/1991 | Sivula et al. |
| 5,065,759 A | 11/1991 | Begemann et al. |
| 5,480,412 A | 1/1996 | Mouchawar et al. |
| 5,496,351 A | 3/1996 | Plicchi et al. |
| 5,496,361 A | 3/1996 | Moberg et al. |
| 5,507,782 A | 4/1996 | Kieval et al. |
| 5,593,431 A | 1/1997 | Sheldon |

(Continued)

OTHER PUBLICATIONS

U.S. Appl. No. 15/140,585, filed Apr. 28, 2016.

(Continued)

*Primary Examiner* — Eugene T Wu

(57) ABSTRACT

An intracardiac ventricular pacemaker having a motion sensor is configured to produce a motion signal including an atrial systolic event and at least one ventricular diastolic event. The pacemaker is configured to set an atrial refractory period, detect a change in a ventricular diastolic event metric and adjust the atrial refractory period in response to detecting the change. The pacemaker sets set an atrioventricular pacing interval in response to detecting the atrial systolic event from the motion signal after expiration of the atrial refractory period.

29 Claims, 10 Drawing Sheets

(56) References Cited

U.S. PATENT DOCUMENTS

| | | | |
|---|---|---|---|
| 5,683,432 A | 11/1997 | Goedeke et al. | |
| 5,693,075 A | 12/1997 | Plicchi et al. | |
| 5,861,011 A | 1/1999 | Stoop | |
| 5,885,471 A | 3/1999 | Ruben et al. | |
| 6,044,297 A | 3/2000 | Sheldon et al. | |
| 6,978,184 B1 | 12/2005 | Marcus et al. | |
| 7,127,289 B2 | 10/2006 | Yu et al. | |
| 7,130,681 B2 | 10/2006 | Gebhardt et al. | |
| 7,569,020 B2 | 8/2009 | Norén et al. | |
| 7,904,155 B2 | 3/2011 | Yu et al. | |
| 8,214,036 B2 | 7/2012 | Casset | |
| 8,233,981 B2 | 7/2012 | Casset | |
| 8,433,409 B2 | 4/2013 | Johnson et al. | |
| 8,532,785 B1 | 9/2013 | Crutchfield et al. | |
| 8,541,131 B2 | 9/2013 | Lund et al. | |
| 8,831,705 B2 | 9/2014 | Dobak | |
| 8,909,329 B2 | 12/2014 | Prakash et al. | |
| 8,923,963 B2 | 12/2014 | Bonner et al. | |
| 8,996,109 B2 | 3/2015 | Karst et al. | |
| 9,272,146 B2 | 3/2016 | Anselmi | |
| 9,278,218 B2 | 3/2016 | Karst et al. | |
| 9,399,140 B2 | 7/2016 | Cho et al. | |
| 2009/0209875 A1* | 8/2009 | Giorgis | A61B 5/02028 600/512 |
| 2010/0125308 A1* | 5/2010 | Casset | A61N 1/368 607/28 |
| 2012/0095521 A1 | 4/2012 | Hintz | |
| 2012/0172892 A1 | 7/2012 | Grubac et al. | |
| 2012/0245853 A1* | 9/2012 | Baumann | A61B 5/02028 702/19 |
| 2013/0325081 A1* | 12/2013 | Karst | A61N 1/36592 607/25 |
| 2014/0121721 A1 | 5/2014 | Ghanem et al. | |
| 2015/0224320 A1 | 8/2015 | Stahmann | |
| 2015/0360036 A1 | 12/2015 | Kane et al. | |
| 2016/0011416 A1 | 1/2016 | Kobayashi | |
| 2016/0015287 A1 | 1/2016 | Anderson et al. | |
| 2016/0015322 A1 | 1/2016 | Anderson et al. | |
| 2016/0015984 A1 | 1/2016 | Demmer et al. | |
| 2016/0015985 A1 | 1/2016 | Cho et al. | |
| 2016/0023000 A1 | 1/2016 | Cho et al. | |
| 2016/0067486 A1 | 3/2016 | Brown | |
| 2016/0067487 A1 | 3/2016 | Demmer et al. | |
| 2016/0067490 A1 | 3/2016 | Carney et al. | |
| 2016/0067500 A1 | 3/2016 | Demmer et al. | |
| 2016/0114161 A1* | 4/2016 | Amblard | A61N 1/365 607/4 |
| 2016/0114162 A1 | 4/2016 | Sheldon et al. | |
| 2016/0114168 A1 | 4/2016 | Demmer et al. | |
| 2016/0114169 A1 | 4/2016 | Sheldon et al. | |
| 2016/0144190 A1 | 5/2016 | Cao et al. | |
| 2016/0144191 A1 | 5/2016 | Sheldon et al. | |
| 2016/0310733 A1 | 10/2016 | Sheldon et al. | |
| 2017/0049325 A1 | 2/2017 | Schmidt et al. | |
| 2017/0173346 A1 | 6/2017 | Kane et al. | |
| 2017/0368347 A1* | 12/2017 | Muessig | A61N 1/3622 |
| 2018/0085588 A1* | 3/2018 | Splett | A61N 1/36578 |
| 2018/0085589 A1* | 3/2018 | Splett | A61N 1/36578 |

OTHER PUBLICATIONS

U.S. Appl. No. 14/934,466, filed Nov. 6, 2015.
U.S. Appl. No. 14/920,228, filed Oct. 22, 2015.
U.S. Appl. No. 14/810,559, filed Jul. 28, 2015.
U.S. Appl. No. 15/280,339, filed Sep. 29, 2016.
U.S. Appl. No. 15/280,538, filed Sep. 29, 2016.
Vitatron Medical b.v. 1996. 3085-616/1, Topaz II, 26 pages.
Vitatron, Clarity DDDR Product Information Manual (US), Nov. 15, 2000, 179 pages.

* cited by examiner

ATRIAL TRACKING IN AN INTRACARDIAC VENTRICULAR PACEMAKER

TECHNICAL FIELD

The disclosure relates to an intracardiac ventricular pacemaker and associated method for detecting atrial events from a motion sensor signal and controlling ventricular pacing delivered by the pacemaker.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing in order to maintain a regular heart rhythm.

SUMMARY

In general, the disclosure is directed to a ventricular pacemaker and techniques for detecting atrial systolic events from a motion sensor signal for controlling atrial-synchronized ventricular pacing by the ventricular pacemaker. A pacemaker operating according to the techniques disclosed herein sets an atrial refractory period and adjusts the atrial refractory period in response to detecting a change in a ventricular diastolic event of the motion sensor signal.

In one example, the disclosure provides an intracardiac ventricular pacemaker, including a pulse generator, a motion sensor and a control circuit. The motion sensor is configured to produce a motion signal comprising an atrial systolic event and at least one ventricular diastolic event. The control circuit is configured to set an atrial refractory period, determine a ventricular diastolic event metric, detect a change in the ventricular diastolic event metric compared to at least one previously determined ventricular diastolic event metric, adjust the atrial refractory period in response to detecting the change, detect the atrial systolic event from the motion signal, and set an atrioventricular pacing interval in response to detecting the atrial systolic event after an expiration of the atrial refractory period. The control circuit controls the pulse generator to deliver a pacing pulse to a ventricle of the patient's heart in response to the atrioventricular pacing interval expiring.

In another example, the disclosure provides a method performed by an intracardiac ventricular pacemaker having a motion sensor. The method includes producing by the motion sensor a motion signal comprising an atrial systolic event and at least one ventricular diastolic event. The method further includes setting by a control circuit of the pacemaker an atrial refractory period, determining by the control circuit a ventricular diastolic event metric, detecting a change in the ventricular diastolic event metric compared to at least one previously determined ventricular diastolic event metric, adjusting the atrial refractory period in response to detecting the change, detecting the atrial systolic event from the motion signal, setting an atrioventricular pacing interval in response to detecting the atrial systolic event after an expiration of the atrial refractory period, and delivering a pacing pulse to a ventricle of the patient's heart via electrodes coupled to the pacemaker in response to the atrioventricular pacing interval expiring.

In yet another example, the disclosure provides a non-transitory computer-readable medium storing a set of instructions which when executed by a control circuit of an intracardiac ventricular pacemaker having a motion sensor, cause the pacemaker to produce by the motion sensor a motion signal comprising an atrial systolic event and at least one ventricular diastolic event. The pacemaker is further caused to set an atrial refractory period, determine by the control circuit a ventricular diastolic event metric, detect a change in the ventricular diastolic event metric compared to at least one previously determined ventricular diastolic event metric, adjust the atrial refractory period in response to detecting the change; detect the atrial systolic event from the motion signal, set an atrioventricular pacing interval in response to detecting the atrial systolic event after an expiration of the atrial refractory period, and deliver a pacing pulse to a ventricle of the patient's heart via electrodes coupled to the pacemaker in response to the atrioventricular pacing interval expiring.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
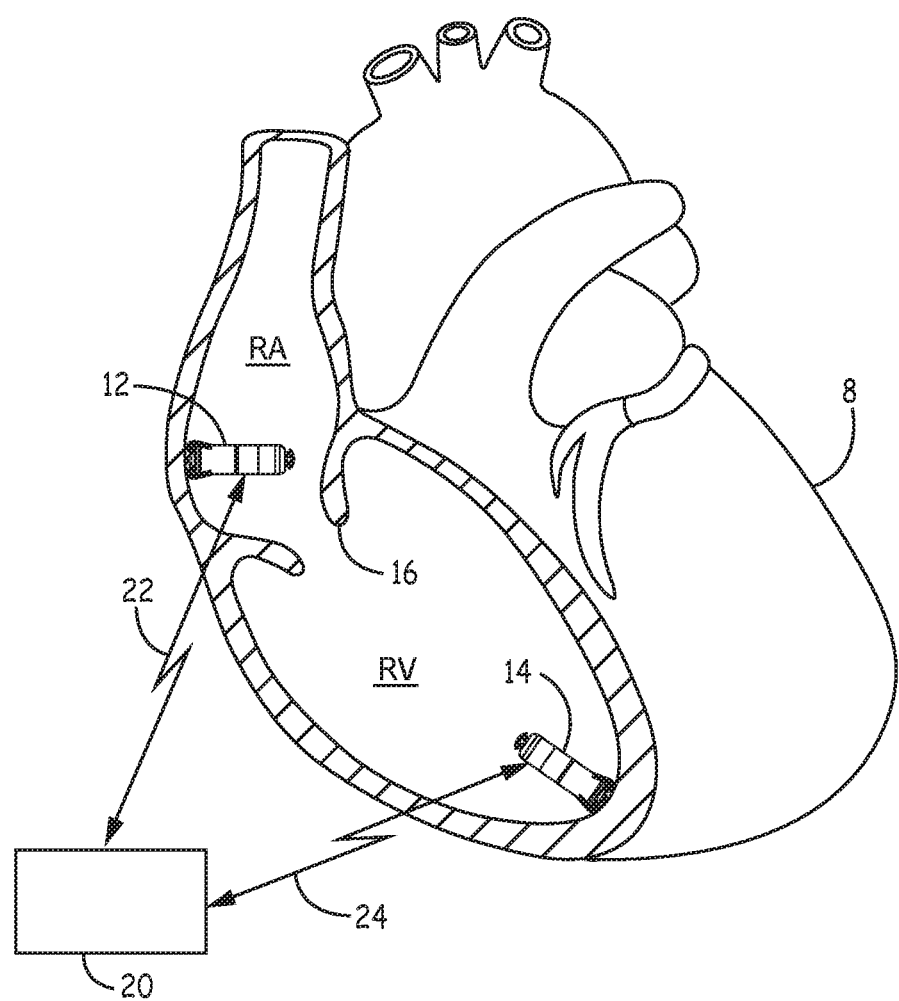
FIG. 1 is a conceptual diagram illustrating an intracardiac pacing system that may be used to sense cardiac electrical signals and motion signals induced by cardiac motion and flowing blood and provide pacing therapy to a patient's heart.

FIG. 1 is a conceptual diagram illustrating an intracardiac pacing system 10 that may be used to sense cardiac electrical signals and motion signals induced by cardiac motion and flowing blood and provide pacing therapy to a patient's heart 8. IMD system 10 includes a right ventricular (RV) intracardiac pacemaker 14 and may optionally include a right atrial (RA) intracardiac pacemaker 12 in some examples. Pacemakers 12 and 14 are transcatheter intracardiac pacemakers which may be adapted for implantation wholly within a heart chamber, e.g., wholly within the RV, wholly within the left ventricle (LV), wholly within the RA or wholly within the left atrium (LA) of heart 8.

In the example of FIG. 1, RA pacemaker 12 is positioned along an endocardial wall of the RA, e.g., along the RA lateral wall or RA septum. RV pacemaker 14 is positioned along an endocardial wall of the RV, e.g., near the RV apex though other locations are possible. The techniques disclosed herein are not limited to the pacemaker locations shown in the example of FIG. 1 and other positions and relative locations in the heart 8 and from each other are possible. For example, a intracardiac ventricular pacemaker 14 may be positioned in the LV for and configured to detect cardiac motion signals and deliver atrial-synchronized ventricular pacing to the LV using the techniques disclosed herein.

Pacemakers 12 and 14 are reduced in size compared to subcutaneously implanted pacemakers and may be generally cylindrical in shape to enable transvenous implantation via a delivery catheter. In other examples, pacemakers 12 and 14 may be positioned at any other location inside heart 8. For example, pacemaker 12 may be positioned outside or within the right atrium or left atrium to provide respective right atrial or left atrial pacing. Pacemaker 14 may be positioned within the right ventricle or left ventricle to provide respective right ventricular or left ventricular pacing and for sensing motion signals by a motion sensor within the ventricular chamber.

Pacemakers 12 and 14 are each capable of producing electrical stimulation pulses, e.g., pacing pulses, delivered to heart 8 via one or more electrodes on the outer housing of the pacemaker. RA pacemaker 12 is configured to sense a cardiac electrical signal from within the RA that may be used to produce an RA intracardiac electrogram (EGM) signal. RV pacemaker 14 is configured to deliver RV pacing pulses and sense an RV cardiac electrical signal using housing based electrodes for producing an RV EGM signal. The cardiac electrical signals may be sensed by the respective pacemaker 12 or 14 using the housing based electrodes that are also used to deliver pacing pulses to the respective RA or RV.

In some examples, a patient may only require RV pacemaker 14 for delivering ventricular pacing. In other examples, depending on individual patient need, RA pacemaker 12 may be required for delivering atrial pacing. The RV pacemaker 14 is configured to control the delivery of ventricular pacing pulses to the RV in a manner that promotes synchrony between the RA activation and the RV activation, e.g., by maintaining a target atrioventricular (AV) interval between atrial events and ventricular pacing pulses. That is, the RV pacemaker 14 controls RV pacing pulse delivery to maintain a desired AV interval between atrial activations (intrinsic or pacing-evoked) corresponding to atrial systole and ventricular pacing pulses delivered to cause ventricular depolarization.

According to the techniques described herein, atrial activations are detected by RV pacemaker 14 from a motion sensor signal that includes motion signals caused by ventricular and atrial events. For example, acceleration of blood flowing into the RV through the tricuspid valve 16 between the RA and RV caused by atrial activation, sometimes referred to as the "atrial kick," is detected by RV pacemaker 14 from the signal produced by a motion sensor, for example an accelerometer, included in RV pacemaker 14. Other motion signals detected by RV pacemaker 14, such as motion caused by ventricular contraction, motion caused by ventricular relaxation, and motion caused by passive filling of the ventricle are described below in conjunction with FIG. 4.

Atrial P-waves that are attendant to atrial depolarization are relatively low amplitude signals in the near-field RV cardiac electrical signal received by RV pacemaker 14 (e.g., compared to the near-field R-wave) and therefore can be difficult to reliably detect from the cardiac electrical signal acquired by RV pacemaker 14. As such, atrial-synchronized ventricular pacing by RV pacemaker 14 may not be reliable when based solely on a cardiac electrical signal received by RV pacemaker 14. According to the techniques disclosed herein, the RV pacemaker 14 includes a motion sensor, such as an accelerometer, and is configured to detect an atrial event corresponding to atrial mechanical activation or atrial systole using a signal from the motion sensor. Ventricular pacing pulses are synchronized to the atrial event that is detected from the accelerometer signal by setting a programmable AV pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event.

A target AV interval may be a programmed value selected by a clinician and is the time interval from the detection of the atrial event until delivery of the ventricular pacing pulse. In some instances, the target AV interval may be started from the time the atrial systolic event is detected based on a motion sensor signal or starting from an identified fiducial point of the atrial event signal. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by RV pacemaker 14 and the motion sensor signal received by RV pacemaker 14.

Pacemakers 12 and 14 may each be capable of bidirectional wireless communication with an external device 20 for programming the AV pacing interval and other pacing control parameters as well as mechanical event sensing parameters utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemakers 12 and 14 using external device 20.

External device 20 is configured for bidirectional communication with implantable telemetry circuitry included in RV pacemaker 14 and RA pacemaker 12 (when present). External device 20 establishes a wireless radio frequency (RF) communication link 22 with RA pacemaker 12 and wireless RF communication link 24 with RV pacemaker 14 using a communication protocol that appropriately addresses the targeted pacemaker 12 or 14. Communication links 22 and 24 may be established using an RF link such as BLUETOOTH®, Wi-Fi, Medical Implant Communication Service (MICS) or other communication bandwidth. In some examples, external device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

External device 20 may display data and information relating to pacemaker functions to a user for reviewing pacemaker operation and programmed parameters as well as EGM signals transmitted from pacemaker 14 or pacemaker 12, motion sensor signals acquired by RV pacemaker 14, or other physiological data that is acquired by and retrieved from pacemakers 12 and/or 14 during an interrogation session.

It is contemplated that external device 20 may be in wired or wireless connection to a communications network via a telemetry circuit that includes a transceiver and antenna or via a hardwired communication line for transferring data to a remote database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in RV pacemaker 14, e.g., after viewing a visual representation of EGM, motion sensor signal and marker channel data.

RA pacemaker 12 and RV pacemaker 14 may or may not be configured to communicate directly with each other. When pacemakers 12 and 14 are configured to communicate with each other, communication may be minimized in order to conserve battery life of the intracardiac pacemakers 12 and 14. As such, communication may not occur on a beat-by-beat basis between the RA pacemaker 12 and RV pacemaker 14 for communicating when the other pacemaker is sensing cardiac events or when it is delivering pacing pulses. As disclosed herein, RV pacemaker 14, however, is configured to detect atrial events as often as beat-by-beat from a motion sensor signal, without requiring communication signals from RA pacemaker 12 to provide atrial event detection for controlling atrial-synchronized ventricular pacing.

Figure 2A:
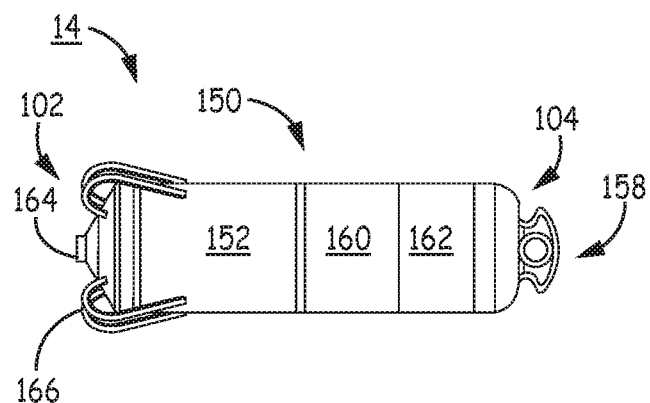
FIG. 2A is a conceptual diagram of the intracardiac ventricular pacemaker shown in FIG. 1.

FIG. 2A is a conceptual diagram of the intracardiac RV pacemaker 14 shown in FIG. 1. RV pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 as a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting ventricular mechanical events and atrial systolic events for timing ventricular pacing pulses as described below.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned, pre-grant publication U.S. 2012/0172892 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 2B:
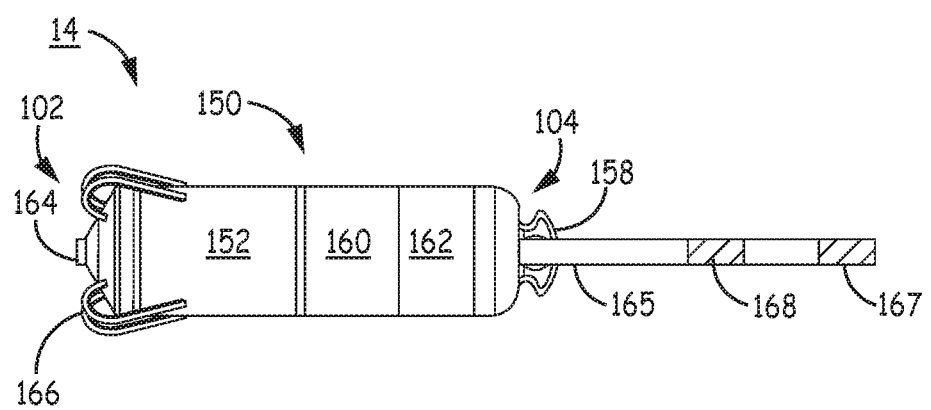
FIG. 2B is a conceptual diagram of another example of the intracardiac ventricular pacemaker shown in FIG. 1.

FIG. 2B is a conceptual diagram of another example of RV pacemaker 14. In FIG. 2B, RV pacemaker 14 includes a proximal sensing extension 165 extending away from housing 150 and carrying a pair of sensing electrodes 167 and 168. The proximal sensing extension 165 may be coupled to the housing 150 for positioning a return sensing electrode 168 or 167 which may be paired with distal electrode 164 at an increased inter-electrode distance compared to the inter-electrode spacing of housing-based electrodes 162 and 164. The increased inter-electrode distance may facilitate sensing of far-field atrial signals such as P-waves attendant to atrial depolarization.

Alternatively, electrodes 167 and 168 may form a sensing electrode pair for sensing atrial P-waves. When distal end 102 is fixed along the RV apex, sensing extension 165 may extend toward the RA thereby positioning electrodes 167 and 168 nearer the atrial tissue for sensing far-field atrial P-waves. One electrode 167 may be coupled to sensing circuitry enclosed in housing 150 via an electrical feedthrough crossing housing 150, and one electrode 168 may be coupled to housing 150 to serve as a ground electrode.

Figure 3:
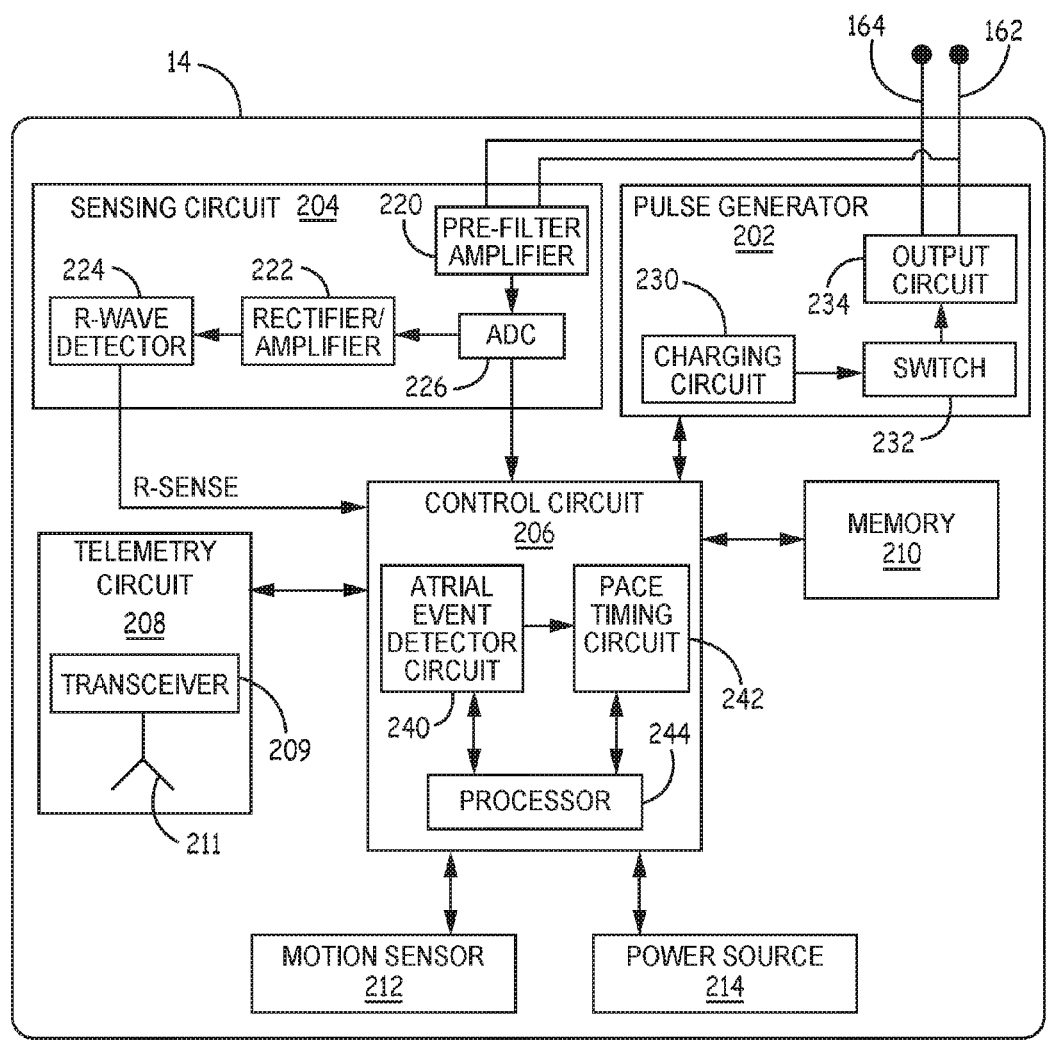
FIG. 3 is a schematic diagram of an example configuration of the pacemaker of FIG. 2A.

FIG. 3 is a schematic diagram of an example configuration of RV pacemaker 14 shown in FIG. 1. Pacemaker 14 includes a pulse generator 202, a sensing circuit 204, a control circuit 206, memory 210, telemetry circuit 208, motion sensor 212 and a power source 214. Motion sensor 212 is implemented as an accelerometer in the examples described herein and may also be referred to herein as "accelerometer 212." Motion sensor 212 is not limited to being an accelerometer, however, and other motion sensors may be utilized successfully in pacemaker 14 for detecting cardiac motion signals according to the techniques described herein. Examples of motion sensors that may be implemented in pacemaker 14 include piezoelectric sensors and micro electro-mechanical systems (MEMS) devices.

Motion sensor 212 may be a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on RV pacemaker 14 due to ventricular and atrial events.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 includes an atrial event detector circuit 240, pace timing circuit 242, and processor 244. Atrial event detector circuit 240 is configured to detect atrial mechanical events from a signal received from motion sensor 212. As described below, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode and for preventing ventricular asystole in the absence of a detected atrial event. R-wave sensed event signals may also be passed to atrial event detector circuit 240 for use in setting ventricular event detection windows and/or atrial event refractory periods, for example as shown and described in conjunction with FIG. 6.

Atrial event detector circuit 240 receives a motion signal from motion sensor 212 and starts an atrial refractory period in response to a ventricular electrical event, e.g., an R-wave sensed event signal from sensing circuit 204 or delivery of a pacing pulse by pulse generator 202. Atrial event detector circuit 240 determines if the motion sensor signal satisfies atrial mechanical event detection criteria outside of the atrial refractory period. The motion sensor signal during the atrial refractory period may be monitored by atrial event detector circuit 240 for the purposes of detecting ventricular mechanical events, which may be used for confirming or validating atrial systolic event detection and/or setting atrial systolic event detection control parameters as further described below, e.g., in conjunction with FIG. 10. As such, ventricular mechanical event detection windows may be set during the atrial refractory period and may be set according to predetermined time intervals following identification of a ventricular electrical event. Atrial event detector circuit 240 may be configured to detect one or more ventricular mechanical events during respective ventricular event detection windows during the atrial refractory period. The timing and detection of the ventricular mechanical events may be used to update the atrial refractory period and/or an atrial systolic detection threshold amplitude and may be used to confirm detection of the atrial systolic event occurring subsequent to expected ventricular mechanical events.

Atrial event detector circuit 240 passes an atrial event detection signal to processor 244 and/or pace timing circuit 242. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. Techniques for controlling atrial-synchronized ventricular pacing using a motion sensor signal are generally disclosed in U.S. Pat. No. 9,399,140, (Yong, et al.), incorporated herein by reference in its entirety.

Pace timing circuit 242 may additionally include a lower rate (LR) pacing interval timer for controlling a minimum ventricular pacing rate in the absence of detected atrial events. For example, if an atrial systolic event is not detected from the motion sensor signal triggering a ventricular pacing pulse at the programmed AV pacing interval, a ventricular pacing pulse may be delivered by pulse generator 202 upon expiration of the LR pacing interval to prevent ventricular asystole and maintain a minimum ventricular rate.

Processor 244 may retrieve other programmable pacing control parameters, such as pacing pulse amplitude and pacing pulse width that are passed to pulse generator 202 for controlling pacing pulse delivery. In addition to providing control signals to pace timing circuit 242 and pulse generator 202 for controlling pacing pulse delivery, processor 244 may provide sensing control signals to sensing circuit 204, e.g., R-wave sensing threshold, sensitivity, various blanking and refractory intervals applied to the cardiac electrical signal, and atrial event detection control signals to atrial event detector circuit 240 for use in detecting and confirming atrial systolic events, e.g., ventricular event detection windows, atrial refractory period, detection threshold amplitudes applied to the motion sensor signal, and any other atrial event detection criteria applied by circuitry included in atrial event detector circuit 240.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or LR pacing interval) and kept closed for a programmed pacing pulse duration to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by pulse generator 202, e.g., by detecting an atrial systolic event by atrial event detector circuit 240 from the motion sensor signal and setting a pacing escape interval timer included in pace timing circuit 242, according to the techniques disclosed herein.

Power source 214 provides power to each of the other circuits and components of pacemaker 14 as required. Control circuit 206 may execute power control operations to control when various circuits or components are powered to perform various pacemaker functions. Power source 214 may include one or more energy storage devices, such as one or more rechargeable or non-rechargeable batteries. The connections between power source 214 and other pacemaker circuits and components are not shown in FIG. 3 for the sake of clarity.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

Figure 4:
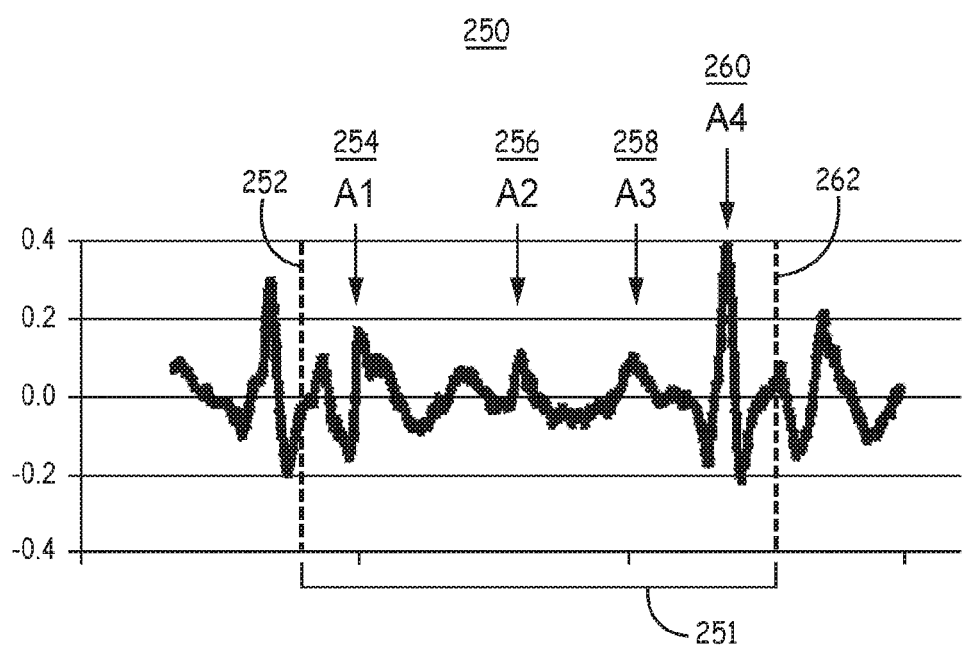
FIG. 4 is an example of a motion sensor signal that may be acquired over a cardiac cycle by a motion sensor included in the intracardiac ventricular pacemaker of FIG. 1.

FIG. 4 is an example of a motion sensor signal 250 that may be acquired by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 250 is implemented as an accelerometer) that occurs during ventricular contraction and marks the approximate onset of ventricular mechanical systole. The A1 event is also referred to herein as a "ventricular contraction event." The A2 event 265 is an acceleration signal that occurs during ventricular relaxation and marks the approximate offset or end of ventricular mechanical systole. The A2 event is also referred to herein as the "ventricular relaxation event." The A3 event 258 is an acceleration signal that occurs during passive ventricular filling and marks ventricular mechanical diastole. The A3 event is also referred to herein as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "atrial systolic event" or merely the "atrial event," and is the atrial systolic event that is detected from motion sensor signal 250 by atrial event detector circuit 240 for controlling pace timing circuit 242 to trigger ventricular pacing pulse delivery by starting an AV pacing interval in response to detecting the A4 event 260. As described below, control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Figure 5:
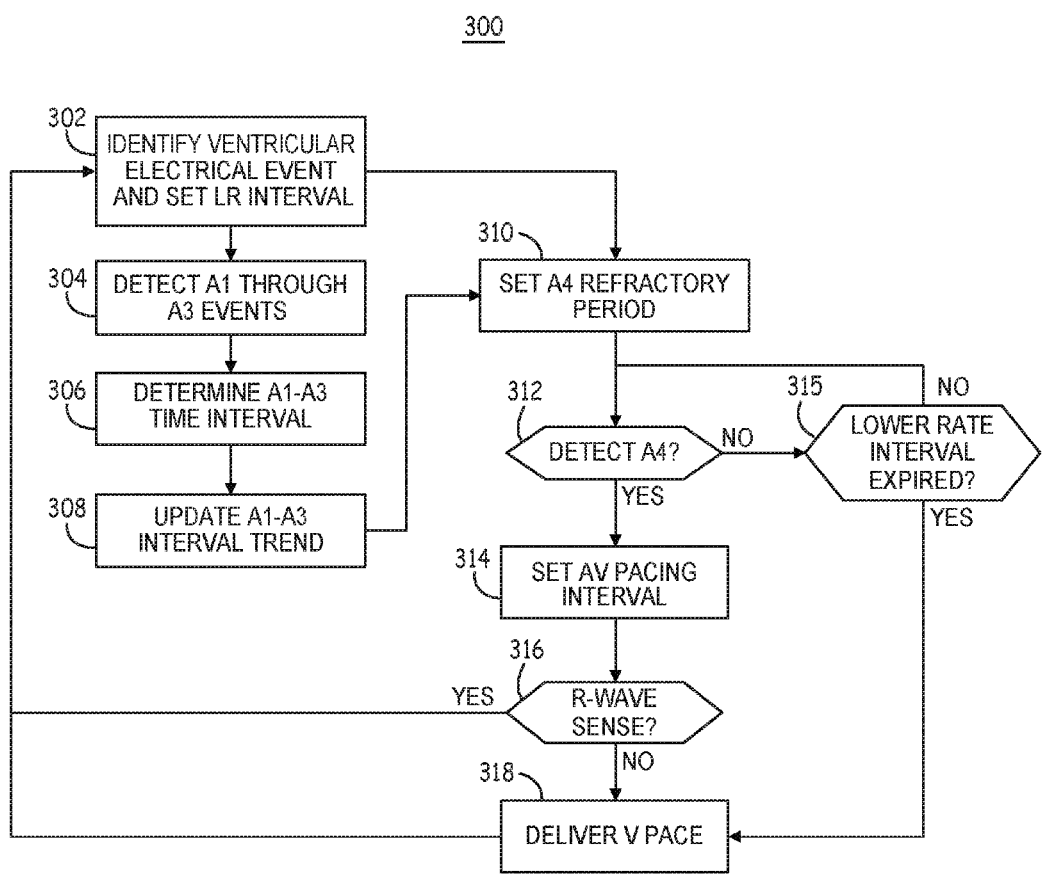
FIG. 5 is a flow chart of one method performed by an intracardiac ventricular pacemaker for detecting an atrial systolic event from a motion sensor signal and controlling ventricular pacing.

FIG. 5 is a flow chart 300 of one method performed by RV pacemaker 14 for detecting the A4 event and controlling ventricular pacing. At block 302, control circuit 206 identifies a ventricular electrical event. The ventricular event may be an R-wave sensed event signal received from sensing circuit 204 or a ventricular pacing pulse delivered by pulse generator 202. Since the ventricular A1, A2 and A3 events may have different characteristics during an intrinsic ventricular rhythm than during a ventricular paced rhythm, the methods described herein for determining amplitudes, time intervals or other characteristics of the A1, A2 and A3 events for use in setting A4 detection control parameters or confirming A4 event detection may be determined for both an intrinsic ventricular rhythm and a ventricular paced rhythm.

For example, as described in conjunction with the flow charts and timing diagrams presented herein, various time intervals, sensing windows, atrial refractory period, and atrial event detection threshold amplitude may be set based on characterizations of one or more of the A1, A2 and A3 events. One set of A4 detection control parameters and characteristics of the A1, A2 and A3 events may be determined and stored for use during episodes of ventricular sensing (ventricular intrinsic rhythm), and another set of A4 detection control parameters and characteristics of the A1, A2 and A3 events may be determined and stored for use during episodes of ventricular pacing.

During ventricular sensing, control circuit 206 may be configured to discriminate a normal sinus R-wave from a premature ventricular contraction (PVC) so that ventricular events identified at block 302 for use in starting a search for the A1 through A4 events from the motion sensor signal do not include PVCs. When a ventricular event, sensed or paced, is identified at block 302 that is not a PVC, pace timing circuit 242 may set an escape interval timer to a ventricular LR pacing interval. If the LR pacing interval expires (as described below in conjunction with block 315), a ventricular pacing pulse may be delivered, asynchronous to atrial activity, in order to maintain some minimum, base ventricular rate.

At block 304, atrial event detector 240 detects the A1 through A3 motion signals. Briefly, atrial event detector 240 may compare the motion sensor signal to one or more pre-determined detection threshold amplitudes during one or more time windows set in response to identifying the ventricular event at bock 302 for detecting the A1 through A3 events. In some examples, the A4 event may also be detected at block 304 to increase confidence in the positive identification of each of the four motion sensor signals A1 through A4 in a given cardiac cycle. In this example, the A1 through A3 events, and optionally A4, may be detected on a beat-by-beat basis.

After the A1 through A3 events are detected, the A1-A3 time interval is determined at block 304 as the time interval from the A1 event detection to the A3 event detection. The A1-A3 time interval may be used to update an A1-A3 interval trend at block 308. For example, a running average A1-A3 time interval may be updated at block 308 using the most recent N A1-A3 time interval measurements, e.g., the most recent three to twelve A1-A3 time intervals.

The A1-A3 time interval is used to set a post-ventricular atrial refractory period at block 310. This atrial refractory period is also referred to herein as an "A4 refractory period" because A4 event detection is inhibited during the atrial refractory period in some examples. When a ventricular electrical event is identified at block 302, atrial event detector 240 may start the atrial refractory period at block 310. The atrial refractory period may be set based on the A1-A3 time interval, e.g., to a percentage longer than or a fixed interval longer than the A1-A3 time interval. For example, the atrial refractory period may be set to be 50 to 150 ms longer than the A1-A3 time interval, though shorter or longer fixed intervals may be added to the A1-A3 time interval for setting the atrial refractory period. The fixed time interval used to set the atrial refractory period may vary depending on heart rate in some examples.

During the atrial refractory period, any motion sensor events that are detected, or cross a detection threshold amplitude, are ignored for the purposes of triggering a ventricular pacing pulse and starting an AV pacing interval. Ventricular mechanical events A1 through A3 may be detected during the atrial refractory period, as indicated at block 304, to determine the A1-A3 time interval and update the A1-A3 interval trend (blocks 306 and 308), either periodically or on a beat-by-beat basis.

At block 312, atrial event detector circuit 240 monitors the motion sensor signal to detect the A4 event after the expiration of the atrial refractory period. If the A4 event is not detected before the LR pacing interval expires (block 315), a ventricular pacing pulse is delivered at block 316 to ensure a minimum ventricular rate, e.g., at least 40 to 60 beats per minute. Furthermore, it is to be understood that if an intrinsic R-wave is sensed before an A4 event is detected, the process of FIG. 5 may return to block 302 where the sensed R-wave is identified as a ventricular electrical event, and control circuit 206 restarts the process of detecting the A4 event on the next ventricular cycle.

If the A4 event is detected before the LR pacing interval expires, control circuit 206 sets the AV pacing interval at block 314 in response to detecting the A4 event. If an intrinsic R-wave is not sensed from the cardiac electrical signal by sensing circuit 204 during the AV pacing interval, "no" branch of block 316, a ventricular pacing pulse is delivered by pulse generator 202 at block 318 upon expiration of the AV pacing interval. The ventricular pacing pulse, if delivered, and otherwise the sensed R-wave, is identified as the next ventricular event at block 302, and the process repeats.

In this way, the A1 through A3 events may be detected from the motion sensor signal on a beat-by-beat (or less frequent) basis for updating the A1-A3 time interval trend used to set the atrial refractory period to provide a high likelihood of positively detecting the A4 event and properly timing a ventricular pacing pulse in synchrony with the atrial event. Other motion sensor signal events A1 through A3 are unlikely to be falsely detected as the A4 event by applying the atrial refractory period set based on the A1-A3 timing.

In some examples, rather than determining an A1-A3 time interval, a time interval to the A2 event may be determined so that the atrial refractory period is set based on the A1-A2 time interval to extend through at least the A2 event and expire before the A3 event. In this example, an A4 detection threshold amplitude may be set higher than an expected A3 event amplitude to allow detection of the A4 event earlier in the ventricular cycle, for example as the atrial rate is increasing. In other cases, the time interval from the identified ventricular electrical event to the A1, A2 or A3 event may be determined and used in setting the atrial refractory period.

In some examples, the process of blocks 304 through 308 is performed periodically rather than on a beat-by-beat basis. For example detection of A1-A3 events during the atrial refractory period may occur on every third cardiac cycle, every eighth cardiac cycle, once a minute or other predetermined schedule for updating the A1-A3 time interval (or other ventricular event time interval as discussed above) used for setting the atrial refractory period at block 310. In some cases, the heart rate, paced or intrinsic, may be monitored and the A1-A3 events may be detected for updating the A1-A3 interval trend when the heart rate changes by more than a predetermined amount. For example, ventricular event intervals between consecutive ventricular events may be determined upon identifying ventricular events at block 302. The ventricular event intervals may be RR intervals between consecutively sensed intrinsic R-waves or VV intervals between consecutively delivered ventricular pacing pulses and may include RV intervals between a sensed intrinsic R-wave and a consecutively delivered pacing pulse and VR intervals between a delivered pacing pulse and a consecutively sensed R-wave. Both the intrinsic heart rate and the paced rate may change as the intrinsic ventricular rate varies and as the RV pacemaker 14 tracks an atrial rate. If the ventricular event interval changes or a trend in the ventricular event interval changes by more than a predetermined amount, the control circuit 206 may perform blocks 304 through 308 to update the A1-A3 interval trend used for setting the atrial refractory period.

In other examples, if the A4 event is not detected at block 312 after the atrial refractory period and before the next ventricular event (intrinsic or paced) is identified at block 302, the control circuit 206 may perform the process of blocks 304 through 306 for a predetermined number of consecutive or non-consecutive cardiac cycles to update the A1-A3 interval trend used to set the atrial refractory period to restore A4 detection.

Figure 6:
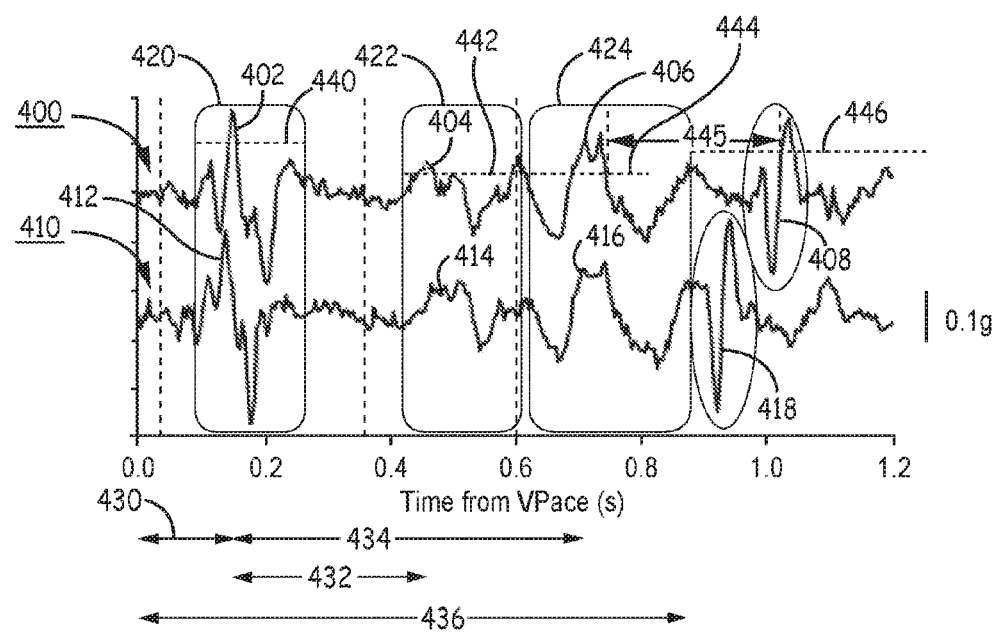
FIG. 6 is an example of a motion sensor signal acquired over two different ventricular cycles.

FIG. 6 is an example of a motion sensor signals 400 and 410 acquired over two different cardiac cycles. A ventricular pacing pulse is delivered at time 0.0 seconds for both cardiac cycles. The top sensor signal 400 is received over one cardiac cycle and the bottom sensor signal 401 is received over a different cardiac cycle. The two signals 400 and 410 are aligned in time at 0.0 seconds, the time of the ventricular pacing pulse delivery.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (occurring during ventricular relaxation) and the A3 events 406 and 416 (occurring during passive ventricular filling) are well-aligned in time. Since the A1, A2 and A3 events are ventricular events, occurring during ventricular contraction, ventricular relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of A1, A2 and A3 events to each other and the immediately preceding ventricular electrical event is expected to be consistent for a given heart rate.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining the atrial refractory period and increasing confidence in reliably detecting A4 events 408 and 418. In some examples, an A1 sensing window 420 may be set based on an expected Vpace-A1 time interval. The Vpace-A1 time interval 430 may be measured when the motion sensor signal 400 or 410 crosses an A1 sensing threshold amplitude 440. The A1 sensing window 420 may be adjusted on the next cardiac cycle based on the Vpace-A1 time interval 430 determined on the current cardiac cycle or a running average Vpace-A1 time interval.

An A2 sensing window 422 may be set based on an expected Vpace-A2 time interval (not explicitly shown but understood to be the total time from 0.0 seconds to an A2 event detection) or an A1-A2 time interval 432 (time from A1 detection to time of A2 detection). The A2 event 404 or 414 may be detected at the time of the first positive-going crossing of an A2 sensing threshold amplitude 442 by the motion sensor signal 400 or 410 during the A2 sensing window 422. The A2 sensing window 422 may be adjusted on the next cardiac cycle based on the Vpace-A2 time interval or A1-A2 time interval 432 determined on the current cardiac cycle.

Similarly, an A3 sensing window 424 may be set based on an expected Vpace-A3 time interval (not explicitly labeled but understood to be sum of time intervals 430 and 434), A1-A3 time interval 434, or A2-A3 time interval (not explicitly labeled but understood to be the time interval from the sensed A2 event 404 or 414 to the sensed A3 event 406 or 416). The A3 event 406 or 416 may be detected during the A3 sensing window 424 when the motion sensor signal 400 or 410, respectively, crosses an A3 sensing threshold amplitude 444. The A3 sensing window 424 may be adjusted on the next cardiac cycle based on the Vpace-A3 time interval, A1-A3 time interval 434, or the A2-A3 time interval determined during the current cardiac cycle.

Each of the sensing windows 420, 422 and 424 may be set based on a history of time intervals determined from a ventricular pacing pulse or sensed intrinsic R-wave to the respective A1 event 402 or 412, A2 event 404 or 414 and A3 event 406 or 416 or based on a history of time intervals between the detected A1, A2 and A3 events or any combination thereof. For example, the A2 sensing window 422 may be set to start based on time intervals measured between a ventricular pacing pulse or sensed R-wave and the detected A1 event. The end of the A2 sensing window 422 may be set to start based on an A1-A2 time interval 432 or based on an A1-A3 time interval 434. It is recognized that numerous methods may be conceived for setting the A1, A2 and A3 sensing windows 420, 422 and 424, respectively, based on the consistency of the expected time intervals between any combinations of the ventricular electrical event (paced or sensed) and subsequent A1, A2 and A3 events. Furthermore, it is contemplated that these sensing windows 420, 422 and 424 may be set according to different control parameters, such as different fixed time intervals added to or subtracted from measured event time intervals depending on whether the ventricular electrical event is a paced or sensed event and/or depending on heart rate. The event time intervals that may be measured and used for setting the onset, offset and duration of the sensing windows 420, 422 and 424 may include any one or combination of the Vpace-A1, Vpace-A2, Vpace-A3, Rsense-A1, Rsense-A2, Rsense-A3, A1-A2, A1-A3, and/or A2-A3 time intervals determined during a paced and/or intrinsic rhythm.

The sensing threshold amplitudes 440, 442 and 444 may be set uniquely during each of the respective sensing windows 420, 422 and 424 or set to a fixed, common value for all sensing windows. The sensing threshold amplitudes 440, 442, and 444 may be fixed or decaying thresholds and may be automatically adjusted thresholds set to starting threshold values based on the peak motion sensor signal amplitude detected during each respective window 420, 422 and 424. The motion sensor signals 400 and 410 are shown as raw signals, but the motion sensor signal may be filtered, amplified and rectified by circuitry included in motion sensor 212 to provide control circuit 206 with a rectified signal that is used to detect the A1 through A4 events.

A post-ventricular, atrial refractory period 436 may be set based on the A1-A3 time interval 434 or based on the Vpace-A3 time interval (sum of Vpace-A1 interval 430 and A1-A3 time interval 434). In some examples, the atrial refractory period 436 ends upon the expiration of the A3 sensing window 424. In other examples, the atrial refractory period 436 ends after the expiration of the A3 sensing window 424. The A4 event 408 or 418 may be detected in response to a crossing of an A4 sensing threshold amplitude 446, e.g., the first positive-going crossing or a last negative-going crossing, by the rectified motion sensor signal.

In some examples, the A4 detection is confirmed when the A1, A2 and A3 events have each been detected during the atrial refractory period 436. If any one of the A1, A2 or A3 events was not detected during the atrial refractory period 436, the A4 event detection based on a crossing of threshold 446 may not be confirmed and not used for starting an AV pacing interval. In other examples, at least one of the A1, A2 or A3 events may be required to be detected during a respective sensing window 420, 422, or 424 on a beat-by-beat basis for confirming an A4 detection after the atrial refractory period 436.

The A1, A2 and/or A3 events sensed during the respective A1 sensing window 420, A2 sensing window 422 and A3 sensing window 424 may be used for updating the atrial refractory period 436 as described in conjunction with FIG. 5 on a beat-by-beat or less frequent basis without requiring positive detection of each of A1, A2, and/or A3 for confirming an A4 detection on each beat. Setting the atrial refractory period based on detection and relative timing of the A1 through A3 events enables the atrial refractory period to be set based on the consistent timing of the ventricular motion sensor signal events so that A4 events may be detected with high reliability even when the timing of the A4 event relative to the A1-A3 events and the preceding ventricular electrical event is variable.

In some examples, an A3-A4 event interval 445 is determined and used for adjusting the A4 refractory period 436. For example, the A3 event 406 may be detected by detecting the last, negative-going crossing of an A3 event detection threshold amplitude 444 during the A3 sensing window 424. The A4 event 408 may be detected by the first positive-going crossing of the A4 event detection threshold amplitude 446 after the expiration of the A4 refractory period 436. The A3-A4 event interval 445 is determined as the time from the A3 event detection and the time of the A4 event detection. This A3-A4 event time may be compared to a previous A3-A4 event time, e.g., compared to one or more preceding A3-A4 event times which may be determined during the respective one or more preceding cardiac cycles or to a running average A3-A4 event time determined from two to five or other predetermined number of previously determined A3-A4 event times. If a change in the A3-A4 event time interval compared to one or more preceding A3-A4 event times is detected, the A4 refractory period 436 may be adjusted. As the A3-A4 event time is detected to shorten or increase, the control circuit 206 may decrease or lengthen the A4 refractory period, respectively, to account for changes in the time interval between the ventricular diastolic event and the atrial systolic event as the atrial rate changes.

Figure 7:
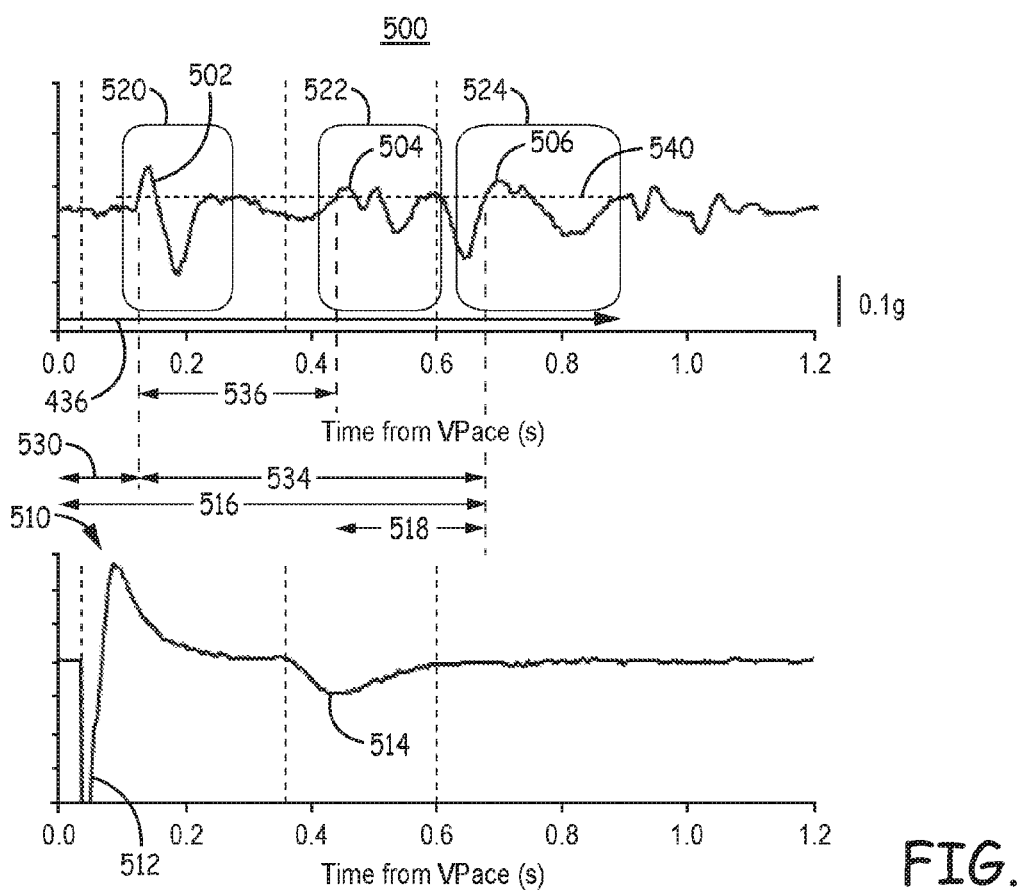
FIG. 7 is an averaged motion sensor signal.

FIG. 7 is an averaged motion sensor signal 500 that may be determined by control circuit 206 by averaging the motion sensor signal acquired over multiple cardiac cycles, e.g., signals 400 and 410 of FIG. 6. The averaged motion sensor signal 500 may represent the average of 3 to 20 or other predetermined number of cardiac cycles. The raw motion sensor signal or a filtered, amplified and/or rectified motion sensor signal may be buffered beginning from a ventricular electrical event, pacing pulse or sensed R-wave, at time 0.0 seconds until the next ventricular electrical event. The buffered motion sensor signal obtained over one cardiac cycle may be averaged with the buffered motion sensor signals obtained over a predetermined number of other cardiac cycles to produce averaged motion sensor signal 500.

A ventricular electrical signal 510 is shown aligned in time with averaged motion sensor signal 500. Ventricular electrical signal 510 may be passed from sensing circuit 204 to control circuit 206 and includes an R-wave 512, which may be an evoked or intrinsic R-wave, and a T-wave 514. R-wave 512 is followed by the ventricular contraction A1 event 502. The ventricular relaxation A2 event 504 occurs during T-wave 514. The passive ventricular filling A3 event 506 occurs after T-wave 514.

Since the A1, A2 and A3 events are ventricular mechanical events, they occur at consistent time intervals relative to each other and relative to ventricular electrical events (R-wave 512 and T-wave 514). As a result, the signal-to-noise ratio of the A1 signal 502, A2 signal 504 and A3 signal 506 is improved in the averaged motion sensor signal 500 compared to the single-cycle motion sensor signals 400 and 410 of FIG. 6. The averaged A1 event 502, A2 event 504 and A3 event 506 have an improved signal-to-noise ratio compared to the A1, A2 and A3 events observed in the motion sensor signal 400 or 410 of a single cardiac cycle as shown in FIG. 6, making A1, A2, and A3 event detection from the averaged motion signal 500 more reliable.

A single event detection threshold amplitude 540 may be defined such that the first positive-going crossing of the threshold 540 by the averaged, rectified motion sensor signal 500 within the A1 sensing window 520, within the A2 sensing window 522 and within the A3 sensing window 524 is detected as the respective A1 event 502, A2 event 504, and A3 event 506. The threshold crossing may be a first, positive-going crossing or a last, negative-going crossing in various examples. Alternatively, unique detection threshold amplitudes may be defined for each sensing window 520, 522 and 524 for detecting the respective A1, A2 and A3 events. The sensing windows 520, 522 and 524 may be initially set according to expected A1, A2 and A3 event timing following the ventricular pacing pulse or R-wave 512 and may be adjusted according to the actual detection time of each respective A1 event 502, A2 event 504, and A3 event 506 based on a threshold crossing. The sensing windows 520, 522 and 524 may be set based on ventricular pacing rate or atrial event rate, e.g., based on A4-A4 event intervals. The sensing windows 520, 522 and 524 may also be set differently following a ventricular pacing pulse than following an intrinsic R-wave sensed event since the timing of the A1, A2 and A3 events and T-wave 514 may be altered during ventricular pacing compared to during an intrinsic ventricular rhythm.

The atrial systolic A4 event timing, which is independent of the ventricular electrical event timing, may be more variable from one cardiac cycle to the next with respect to the ventricular electrical and mechanical events, e.g., as shown by the relative timing of the A4 events 408 and 418 of signals 400 and 410 (FIG. 6). As a result, the A4 signal is largely attenuated in the averaged motion signal 500 in FIG. 7. The improved signal-to-noise ratio of the A1 through A3 events and attenuation of the A4 event in the averaged motion signal 500 enables control circuit 206 to reliably detect the signal averaged A1 event 502, A2 event 504 and A3 event 506 for determining one or more ventricular event time intervals for use in setting A1, A2 and A3 detection windows 420, 422, and 424, respectively, setting detection threshold amplitudes for detecting the A1, A2, A3 and/or A4 events, and/or setting atrial refractory period 436 used on a beat-by-beat basis for A4 event detection as shown in FIG. 6.

For example, a ventricular R-wave or pacing pulse to A1 time interval 530, an A1-A3 time interval 534, A1-A2 time interval 536, a ventricular R-wave or pacing pulse to A3 time interval 516, and/or a T-wave to A3 time interval 518 or any combination thereof may be determined by control circuit 206 from the averaged motion signal 500 and the cardiac electrical signal 510. The atrial refractory period 436 is started upon delivering a ventricular pacing pulse or sensing an intrinsic R-wave. The atrial refractory period 436 may be set to expire after a predetermined time interval, e.g., 30 to 100 ms, after the A3time interval 516. For instance, if time interval 516 is 700 ms, the atrial refractory period 436 may be set to expire 750 ms after the ventricular pacing pulse or sensed R-wave that started the atrial refractory period. Instead of using a time interval ending with the A3 event detection, a time interval ending with the A2 event detection may be determined and used in controlling the duration of the atrial refractory period 436. As described above, the A2 event, which occurs during T-wave 514, is an indicator of the end of ventricular mechanical systole and the onset of ventricular mechanical diastole. The A3 event occurs during ventricular mechanical diastole, during the passive ventricular filling phase. As such the timing of the A2 event 504 or the timing of the A3 event 506 relative to another ventricular electrical event (ventricular pacing pulse, R-wave 512, or T-wave 514) may be used for controlling the duration and expiration time of atrial refractory period 436. In other words, the timing of a ventricular mechanical diastolic event, A2 event 504 or A3 event 506, may be determined and used to set the atrial refractory period 436 that is applied on a beat-by-beat basis for detecting A4 events.

The T-wave 514 may be sensed by sensing circuit 206 on a beat-by-beat basis by control circuit 206 or by sensing circuit 204 from cardiac electrical signal 510. The T-wave 514 may be sensed at a maximum peak amplitude of a rectified cardiac electrical signal or a maximum absolute peak amplitude in a non-rectified cardiac signal received by control circuit 206 from sensing circuit 204. Alternatively, T-wave 514 may be sensed by sensing circuit 204 in response to the cardiac electrical signal crossing a T-wave sensing threshold amplitude after the ventricular pacing pulse or R-wave sensed event signal. In some cases, a T-wave sensing window may be applied after the R-wave sensed event signal or a delivered pacing pulse to facilitate T-wave sensing.

The T-wave 514 may be sensed during the atrial refractory period 436. Control circuit 206 may terminate the atrial refractory period 436 at a predetermined time interval after sensing T-wave 514. For instance if the T-wave to A3 time interval 518 is determined to be 150 ms from the averaged motion signal 500, control circuit 206 may terminate the atrial refractory period 436 at 180 ms after sensing the T-wave to promote reliable sensing of the A4 event.

Atrial event detector circuit 240 may be a processor-based circuit that determines the averaged motion sensor signal 500 over multiple cardiac cycles, detects A1, A2 and A3 events 502, 504, and 506 from the averaged motion sensor signal 500, and sets the atrial refractory period 436 based on the timing of at least one ventricular mechanical diastolic event, e.g., the A3 event 506, detected from the average motion sensor signal 500. In other examples, the A2 event is used as a ventricular diastolic mechanical event for marking the approximate timing of the onset of ventricular diastole. The A4 event, e.g., event 408 or 418 (FIG. 6) may be detected on a beat-by-beat basis from the non-averaged motion sensor signal after the atrial refractory period 436 expires.

Figure 8:
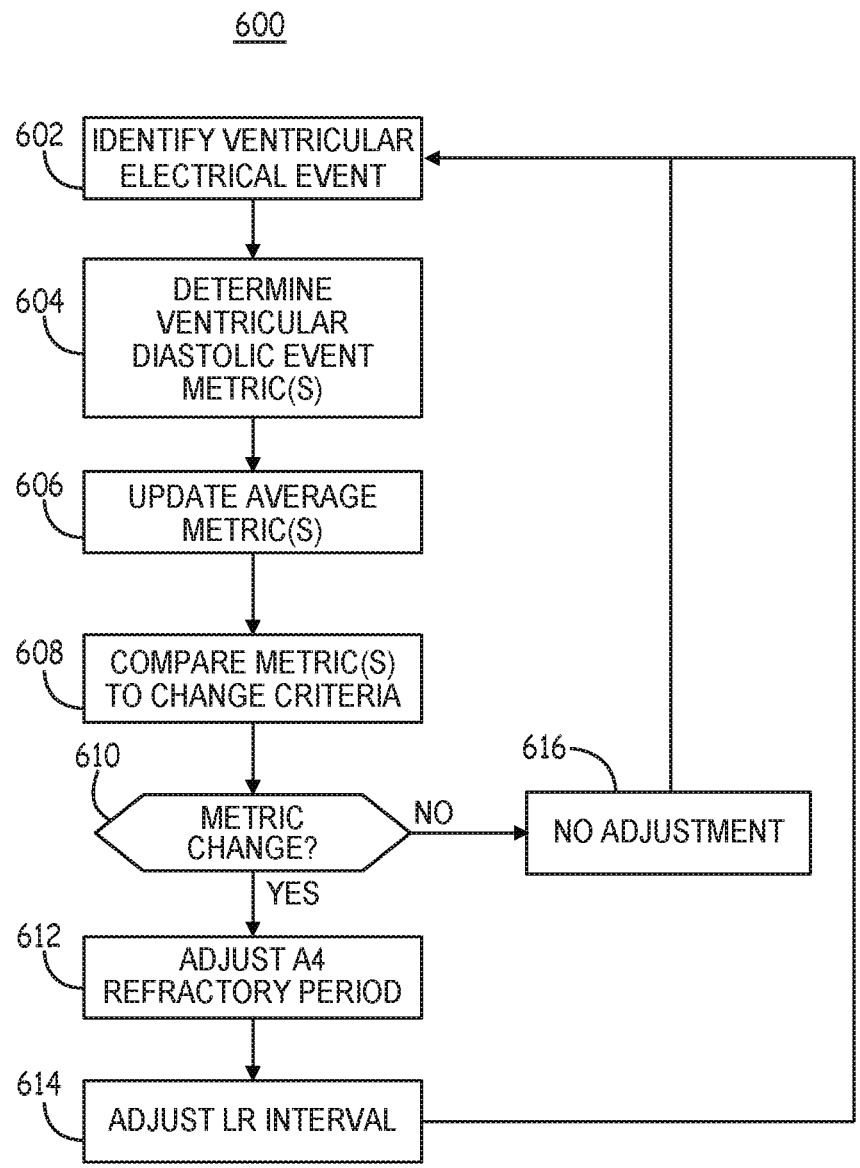
FIG. 8 is a flow chart of a method performed by an intracardiac ventricular pacemaker for controlling an atrial refractory period.

FIG. 8 is a flow chart 600 of a method performed by RV pacemaker 14 for controlling the A4 refractory period. The time interval from a ventricular systolic event (electrical or mechanical) to a subsequent ventricular diastolic mechanical event is expected to shorten when the intrinsic heart rate is about to or is increasing. Tracking a change in a time interval expiring on a ventricular diastolic mechanical event, e.g., ending on the A2 event or the A3 event, allows the A4 refractory period to be adjusted to maintain reliable sensing of the A4 events across heart rate changes.

The process of flow chart 600 may be performed on a periodic basis, on a beat-by-beat basis, or triggered in response to a change in the rate of A4 events, triggered in response to a loss of A4 event detections, triggered in response to detecting an increase in patient activity, triggered in response to detecting a change in patient posture, or in response to another indicator of a possible change in heart rate. The process of flow chart 600 may also be performed upon pacing mode switching, e.g., from a non-atrial tracking pacing mode such as VVI or VDI to an atrial tracking pacing mode such as VDD, and/or may be performed periodically when pacing in a non-atrial tracking mode, such as a VVI(R) pacing mode, for use in adjusting a ventricular LR pacing interval.

At block 602, a ventricular electrical event is identified, which may be a sensed intrinsic R-wave or delivered ventricular pacing pulse. One or more ventricular diastolic event metrics are determined at block 604. In various examples, A2 event metrics and/or A3 event metrics are determined at block 604. For example, one ventricular diastolic event metric determined at block 604 may be an A3-A4 time interval, e.g., A3-A4 time interval 445 shown in FIG. 6. In other examples, the ventricular diastolic event metric(s) is/are determined as A2 event metrics. It is to be understood that one or more ventricular diastolic event metrics may be determined at block 604 as one or more A2 event metrics, one or more A3 event metrics, or any combination of one or more A2 event metrics and one or more A3 event metrics. A diastolic event metric may be a time intervals beginning or ending on the A2 event or A3 event, an event amplitude, or other event feature.

Since the ventricular diastolic events may occur at a different time during paced ventricular cycles than during intrinsic ventricular cycles, and/or have a different amplitude or morphology, the process of flow chart 600 may be performed during a stable, intrinsic heart rhythm for establishing ventricular diastolic event metrics of an intrinsic rhythm and during a paced ventricular rhythm to establish a second set of ventricular diastolic event metrics of a paced rhythm.

In one example, at least an A2 event time interval is determined at block 604 as a ventricular diastolic event metric. The A2 event time interval may be determined as the time interval from an intrinsic sensed R-wave to an A2 event detection, a ventricular pacing pulse to an A2 event detection, or an A1 event detection to an A2 event detection. In other examples, one or more other A2 event metrics may be determined such as an A2 event amplitude. At block 606, the A2 metric(s) determined at block 604 for the current ventricular cycle are used to update an average A2 metric. For example, an A2 event metric may be determined as the A2 event time interval, which is used to update a running average of a predetermined number of A2 event time intervals, e.g., a running average of three to twenty event time intervals, at block 606.

As described below, the ventricular diastolic event metric(s) are used for adjusting the A4 refractory period and/or the ventricular LR pacing interval. In some examples, an average metric determined at block 606 is stored for the current heart rate, which may be determined based on detected A4 event time intervals. An average A2 metric may be stored for each one of multiple heart rates or heart rate ranges as A2 event metric data is accumulated so that the average A2 event metric(s) are available for use in making adjustments to the A4 refractory period and/or the LR pacing interval as the atrial rate changes (e.g., as determined from A4 event intervals) without having to repeat the determination of average A2 metrics.

At block 608, the ventricular diastolic event metric is compared to change criteria for detecting a change in the ventricular diastolic event metric compared to at least one previously determined ventricular diastolic event metric. For example, an updated averaged A2 metric(s) may be compared to change criteria at block 608 for detecting an impending change in heart rate. In some cases, the currently determined most recent A2 metric is compared to the updated average A2 metric to determine if a threshold change in the A2 metric has occurred. In other examples, the average A2 metric may be compared to a previous average A2 metric or to a predetermined threshold to determine if a change in the A2 metric has occurred indicative of an imminent or needed change in heart rate. For example, the A2 vent time interval may decrease by 10% or other threshold change as a predictive indicator that the heart rate is going to increase, or needs to increase in response to an increased patient metabolic demand. As a result the A4 event is expected to shift earlier in the ventricular cycle warranting an adjustment to the A4 refractory period.

If the control circuit 206 determines that change criteria are not satisfied, an A2 metric change is not detected at block 610, and no adjustment is made to the A4 refractory period or any other A4 event detection control parameters. If the change criteria are met at block 608, an A2 metric change is detected at block 610, and the control circuit 206 adjusts the A4 refractory period at block 612. If the A2 event time interval has decreased, the A4 refractory period is decreased; if the A2 event time interval has increased, the A4 refractory period is increased.

In this example, the A4 refractory period may initially be set based on an A3 time interval as described above in conjunction with FIG. 5. The A3 time interval may be determined on a beat-by-beat basis or from an averaged motion sensor signal, e.g., as described in conjunction with FIG. 7. The A4 refractory period initially set based on the A3 time interval is adjusted based on changes in the A2 event metric, used as an indicator of an expected change in heart rate, which may move the A4 event earlier or later in the ventricular cycle. Adjustments to the A4 refractory period may be performed by control module 206 by increasing or decreasing the A4 refractory period from a current value to an adjusted value by increasing or decreasing the A4 refractory period by one or more predetermined step changes. The size of the step change may be based on the amount of change detected in the A2 metric. For example, if the A2 event time interval changes by up to 15% compared to at least one preceding A2 event time interval or compared to the updated average A2 event time interval, the A4 refractory period may be adjusted by 10 ms. If the A2 event time interval changes by 15 to 30% compared to at least one preceding A2 event time interval or compared to the updated average A2 event time interval, the A2 event time interval may be adjusted by 20 ms. These examples are illustrative in nature, and it is understood that the amount of change in the A2 event metric and corresponding size of the adjustment to the A4 refractory period may be based on clinical and/or individual patient data.

In some examples, control circuit 206 adjusts the lower rate (LR) pacing interval at block 614, which may be a temporary LR pacing interval that is shorter than a minimum or base pacing rate interval, in response to detecting the A2 metric change. A permanent LR pacing interval may be programmed and stored in memory 210 corresponding to a permanent lower pacing rate which is the minimum or base pacing rate, e.g., 40 to 60 pulses per minute. The LR pacing interval may be adjusted from the permanent LR pacing interval to a temporary pacing interval based on a sensor indicated pacing rate determined from a patient physical activity metric, which may also be determined from the motion sensor signal. The permanent or a temporary SIR-based LR pacing interval may be adjusted based on a change in the A2 metric.

For example, if the A2 event time interval decreases, it is anticipated that the patient's intrinsic heart rate is expected to rise. As such, the LR pacing interval set at block 302 of FIG. 5 may be shortened to provide a faster ventricular pacing rate in the absence of A4 event detection. The paced or sensed atrial rate may increase to meet an increased patient metabolic demand. If A4 events are not detected for tracking an accelerating atrial rate, a decrease in the A2 event time interval is used as an indication for a need for a higher heart rate. As such, the LR pacing interval is decreased at block 614 to provide a faster pacing rate. If the A2 event time interval increases, the LR pacing interval may be increased at block 614 based on the change in the A2 event metric. The LR pacing interval may be adjusted based on one, two or more average A2 metrics stored for different heart rates in some examples so that the LR pacing interval matches the heart rate that is stored with the corresponding average A2 metric value.

In some instances, therefore, the A4 refractory period and the LR pacing interval may be increased and decreased together as changes in the A2 metric are detected. In other examples, the adjustments to the LR pacing interval may be made less frequently by requiring a higher threshold change in the A2 metric before the LR pacing interval is adjusted than the threshold change required to adjust the A4 refractory period in response to an A2 metric change.

Changes to the A4 refractory period and LR interval in the method of flow chart 600 have been described based on detecting changes in an A2 event time interval as an indicator of an imminent change in heart rate. It is contemplated that an A3 event time interval may be used in addition to or instead of an A2 event time interval for detecting an expected change in heart rate and adjusting the A4 refractory period and/or LR pacing interval in response to the detected change.

Figure 9:
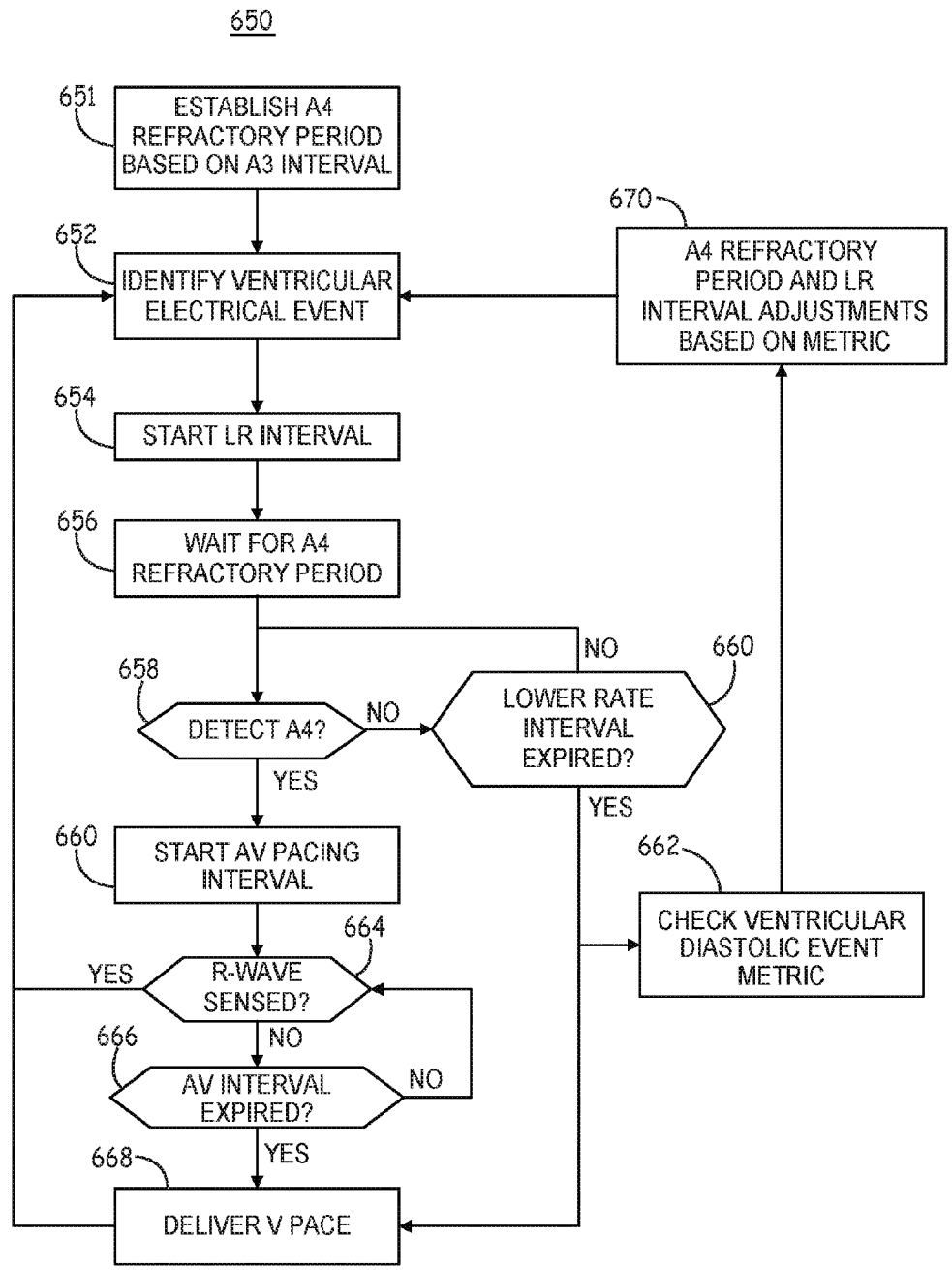
FIG. 9 is a flow chart of a method for controlling ventricular pacing by an intracardiac ventricular pacemaker according to another example.

FIG. 9 is a flow chart 650 of a method for controlling ventricular pacing by RV pacemaker 14 according to another example. At block 651, the A4 refractory period is initially established based on measurements of an A3 interval, e.g., an A1-A3 interval or a ventricular electrical event to an A3 interval, as described in conjunction with FIG. 5. The A4 refractory period may be set to a time interval that is expected to expire after an expected A3 event time. In some examples, the A4 refractory period may be set to a time interval that is expected to expire before the A3 event time but after the A2 event time in which case an adjustable, decaying or multi-level A4 event detection threshold amplitude may be used for detecting high amplitude A4 events that have become fused with the A3 event. Techniques disclosed herein for adjusting the A4 refractory period may be combined with techniques for setting an A4 refractory period and detecting A4 events that may become fused with the A3 event as generally disclosed in U.S. Pat. Application Publication No. 2018/0085588 (Splett, et al.), incorporated herein by reference in its entirety.

At block 652, a ventricular electrical event, paced or sensed, is identified by control circuit 206. Control circuit 206 starts the ventricular LR pacing interval at block 654 and starts the A4 refractory period at block 656. After expiration of the A4 refractory period, the control circuit 206 waits for an A4 event to be detected at block 658, for example based on an A4 detection threshold amplitude crossing of the motion sensor signal. If the A4 event is detected, "yes" branch of block 658, the pace timing circuit 242 starts the AV pacing interval at block 660.

If an intrinsic R-wave is sensed by sensing circuit 204 (block 664), before the AV pacing interval expires, the process returns to block 652 and identifies the sensed R-wave as the next ventricular electrical event. If the AV pacing interval expires at block 666 without an R-wave sensed event signal produced by the sensing circuit 204, the scheduled ventricular pacing pulse is delivered at block 668. The ventricular pacing pulse is identified as the next ventricular electrical event at block 652 and the process repeats.

In some instances, the LR pacing interval started at block 654 may expire before an A4 event is detected. An A4 event may go undetected if it occurs during the A4 refractory period due to an increase in the intrinsic atrial rate or if it occurs later than the expiration of the LR pacing interval due to a decrease in the intrinsic atrial rate when the ventricular LR pacing interval has been shortened, e.g., to support rate responsive pacing. If the LR pacing interval expires without an A4 event detection ("yes" branch of block 660), a ventricular pacing pulse is delivered at block 668 and a ventricular mechanical diastolic event metric is checked at block 662 in response to a ventricular in response to the A4 event being undetected.

The ventricular mechanical diastolic event metric may be the A2 event time interval, the A3 event time interval, the amplitude of the A2 event or another metric of the A2 event, the A3event, or any combination of A2and/or A3event metrics. The event metric may be checked using the techniques described in conjunction with FIG. 8. For example, a running average A2 event time interval may be updated on a beat-by-beat basis in parallel to the operations of flow chart 650 and compared to a current A2 event time interval determined from the current ventricular cycle or from the next ventricular cycle. If the A2 event time interval has changed, the A4 refractory period and/or the LR interval may be adjusted based on the A2 event time interval change at block 670. The A4 refractory period and the LR pacing interval may be shortened in response to the A2interval decreasing or increased in response to the A2 interval increasing. The adjustment to the A4 refractory period and/or LR pacing interval may be proportional to the detected change in the A2 event time interval. The adjusted A4 refractory period and/or adjusted LR pacing interval are started at blocks 654 and 656, respectively, in response to the pacing pulse delivered at block 668, which is identified as the next ventricular electrical event (block 652).

In this way, if the LR pacing interval was causing ventricular pacing in advance of the A4 event during a slowing atrial rate, the LR pacing interval is increased to allow more time for detecting the A4 event. The A4 refractory period may be increased appropriately based on the A2 event time interval change. If an increase in atrial rate has occurred, A4 event detection is promoted by shortening the A4 refractory period to allow earlier detection of the A4 event. A shortened LR pacing interval provides ventricular pacing at a faster rate even when the A4 event is under-detected to support an increased metabolic demand as evidenced by the shortened A2 event time interval.

Figure 10:
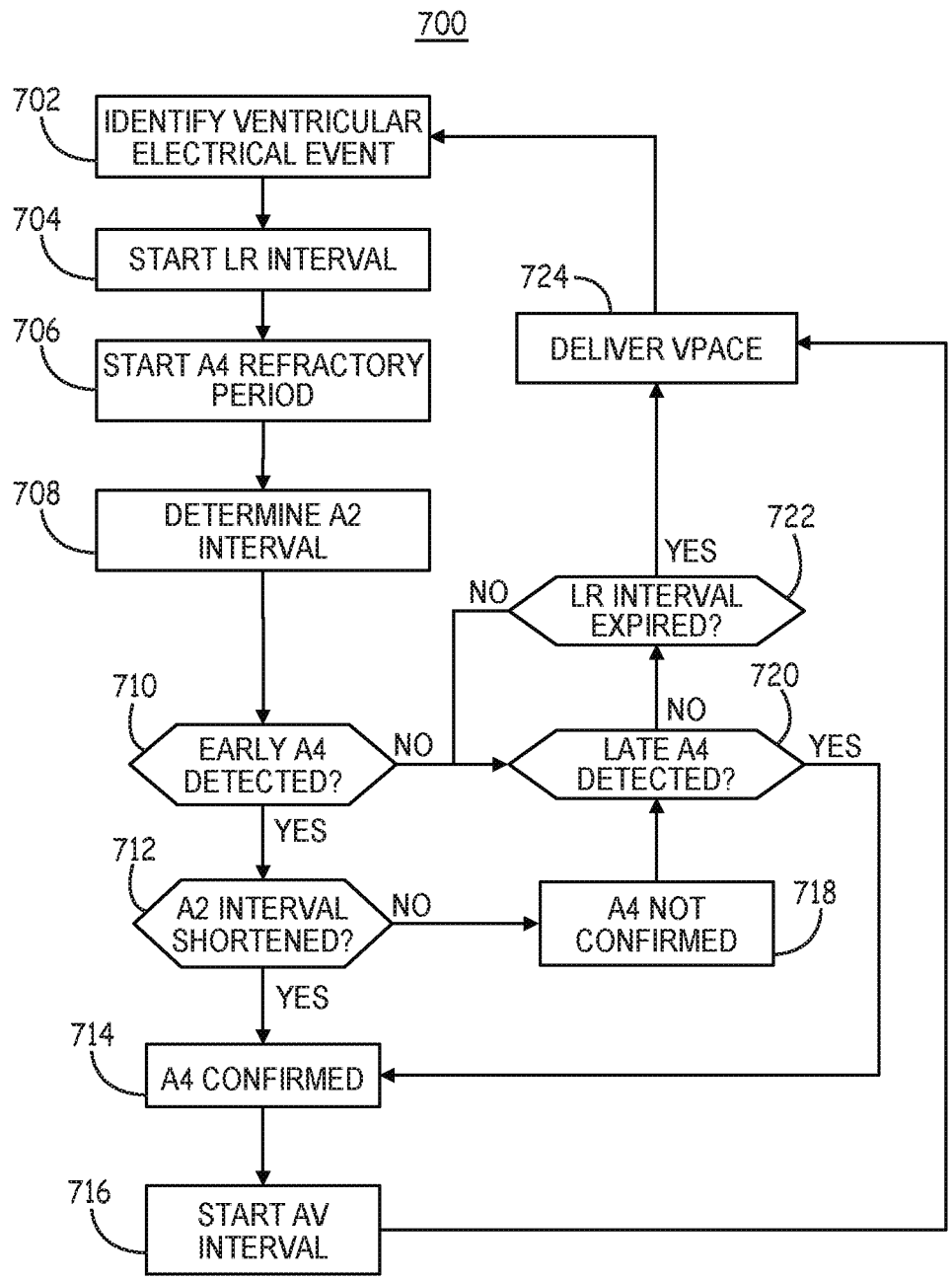
FIG. 10 is a flow chart of a method for monitoring for atrial mechanical systolic events by an intracardiac ventricular pacemaker according to another example.

FIG. 10 is a flow chart 700 of a method for monitoring for A4 events by RV pacemaker 14 according to another example. At block 702, a ventricular electrical event, paced or sensed, is identified. The LR pacing interval and the A4 refractory period are started at blocks 704 and 706 respectively. In this example, the A4 refractory period may be set to expire after an expected A2 event time and before, at or after the expected time of the A3 event. As the atrial rate increases, the A4 event may arrive earlier in the ventricular cycle, close in time to the A3 event or even concomitant with the A3 event causing a fused A3/A4 event signal. In order to maintain A4 event detection, the A4 refractory period may be set to a relatively short time period to enable detection of relatively early A4 events.

The A2 event time interval is determined at block 708 by control circuit 206 by detecting the A2 event from the motion sensor signal during the A4 refractory period and determining the time since the ventricular electrical event until the A2 event detection. In other examples, the A1 event may be detected, and an A1-A2 event time interval may be determined at block 708.

At block 710, control circuit 206 determines if an A4 event is detected early after the A4 refractory period. For instance if the A4 event is detected within a predetermined time window of the expiration of the A4 refractory period, the A4 event is detected as an early A4 event. The predetermined time window may be an A3 event time window defining a window of time that the A3 event is expected to occur. In other examples, a suspected A4 event may be detected during the A4 refractory period if the motion sensor signal crosses an A4 event detection threshold amplitude. This suspected A4 event may be preliminarily detected as an early A4 event if the detection threshold amplitude is crossed during the A4 refractory period.

If an early A4 event is detected based on early A4 event detection criteria, control circuit 206 determines if the A2 event time interval has shortened at block 712. The A2 event time interval determined at block 708 may be compared to the most recent preceding A2 event time interval, to a predetermined number of preceding A2 event time intervals, to a running average A2 event time interval, or to a predetermined threshold to detect A2 event time interval shortening at block 712.

If the A2 event time interval has shortened based on the criteria applied at block 712, the early A4 event detection is confirmed at block 714. If the A2 event time interval has shortened, an indicator of an increasing or imminently increasing heart rate, a relatively early A4 event can be expected. Control circuit 206 starts an AV pacing interval at block 716 to synchronize the next ventricular pacing pulse with the detected atrial systolic A4 event. When the AV pacing interval is started, the LR pacing interval may be stopped to allow the timing of the ventricular pacing pulse to be controlled by the AV pacing interval. The AV pacing interval started at block 716 may be adjusted based on the A2 interval shortening determined at block 712, e.g., according to the methods described in conjunction with FIG. 8.

If the A2 event time interval is not determined to be shortened at block 712, the early A4 event detection is not confirmed at block 718. The early A4 event detection may be a signal caused by patient physical activity or other motion sensor signal noise. The AV pacing interval is not started if the early A4 event is not confirmed. The LR pacing interval is allowed to continue running. Control circuit 206 may continue to monitor for a later A4 event signal at block 720.

A late A4 event may be detected at block 720 based on criteria applied by control circuit 206 for detecting a late A4 event. For example, if the motion sensor signal crosses an A4 event detection threshold amplitude after the A4 refractory period expires, the A4 event is detected as a late A4 event. In other examples, a threshold amplitude crossing after a predetermined time interval after the expiration of the A4 refractory period, e.g., after an A3 event window expires, a late A4 event detection is made. If a late A4 event detection is detected at block 720, the A4 event is confirmed at block 714 based on the relatively "late" timing of the A4 event according to the criteria applied at block 720. An AV pacing interval is started at block 716. The A2 event timing may not be checked for confirming the late A4 event. The A4 refractory period and A4 detection threshold amplitude may be considered to be properly set for detecting at true A4 event. If an A4 event is detected and the subsequent AV pacing interval expires, a ventricular pacing pulse is delivered at block 724.

If an early A4 event is detected but not confirmed and/or no late A4 event is detected, the LR interval expires without an A4 event being detected ("yes" branch of block 722). A ventricular pacing pulse is delivered at block 724 at the LR pacing interval. While not shown explicitly in FIG. 10, it is recognized that if an intrinsic R-wave is sensed by sensing circuit 204 during the LR pacing interval or during the AV pacing interval, the scheduled pacing pulse is withheld, and the process returns to block 702. The sensed R-wave is identified as the next ventricular electrical event.

Figure 11A:
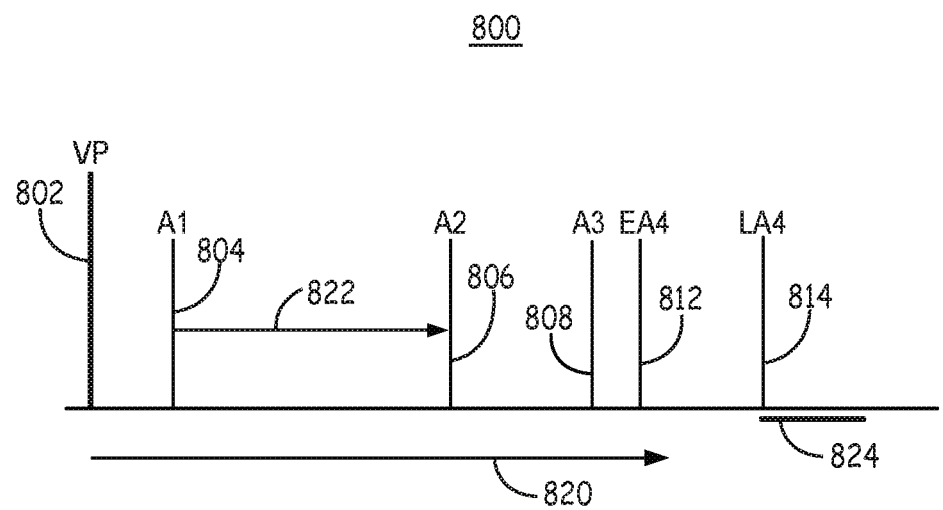
FIG. 11A is a timing diagram depicting one method performed by an intracardiac ventricular pacemaker for distinguishing early and late atrial systolic events detected from a motion sensor signal.

FIG. 11A is a timing diagram 800 depicting one method performed by pacemaker 14 for distinguishing early and late A4 events. In the method of FIG. 10, the A4 refractory period set at block 706 may be set based on an expected time of the A3 event, e.g., as described in conjunction with FIG. 5, and may be adjusted in response to changes in the A2 event time interval as described in conjunction with FIG. 8. The A4 refractory period may expire before, at or later than an expected time of the A3 event in various instances. The distinction between an "early" A4 event detection and a "late" A4 event detection may be based on the expiration time of the A4 refractory period when it is set to expire later than the expected A3 event time.

In FIG. 11A, a ventricular pacing pulse 802 is identified as a ventricular electrical event and starts an A4 refractory period 820 set to expire after an expected time of the A3 event 808. An A2 event 806 is detected during the A4 refractory period 820. In some cases, the A1 event 804 is also detected during the A4 refractory period and used to determine the A2 event time interval 822. In other examples, the A2 event time interval may be measured from the ventricular electrical event VP 802 to the A2 event 806.

The A3 event 808 may be detected during the A4 refractory period based on a motion sensor signal threshold amplitude crossing so that the next event detected from the motion sensor signal can be identified as an A4 event with increased confidence when one, two or all three of the preceding ventricular A1, A2 and A3 events have been detected during the A4 refractory period 820. Detection of the A3 event, however, may not be required before detecting the A4 event.

In the example shown, an A4 event 812 is detected before the expiration of the A4 refractory period 820 and is therefore identified as an early A4 event (EA4). The A4 event 812 may be detected based on a motion sensor signal crossing of the A4 event detection threshold amplitude, which may be a decaying or multi-level threshold having a higher amplitude during the A4 refractory period 820 than after the A4 refractory period 820. In order to confirm the early A4 event 812 detected during the A4 refractory period 820, the A2 event time interval 822 is compared to A2 interval shortening criteria. For example, A2 event time interval 822 may be compared to one or more preceding A2 event time intervals, a running average A2 event time interval, or other threshold for detecting A2 event time interval shortening.

If A2 event time interval shortening is detected, justifying the early occurrence of the A4 event, the early A4 event 812 is confirmed as the A4 event, and an AV pacing interval is started. If the A2 event time interval 822 is not determined to be shortening, the early A4 event 812 is not confirmed. The LR pacing interval started upon VP 802 continues to run as described in conjunction with FIG. 10; no AV pacing interval is started.

An A4 event detected after expiration of the A4 refractory period 820 is detected as a late A4 event (LA4) 814. When the late A4 event 814 is detected outside the A4 refractory period, no confirmation of the A4 event is required based on the A2 event time interval. The LR pacing interval may be cancelled, and a pacing escape timer or counter included in pace timing circuit 242 may be set to the AV pacing interval 824 in response to the late A4 event 814.

Figure 11B:
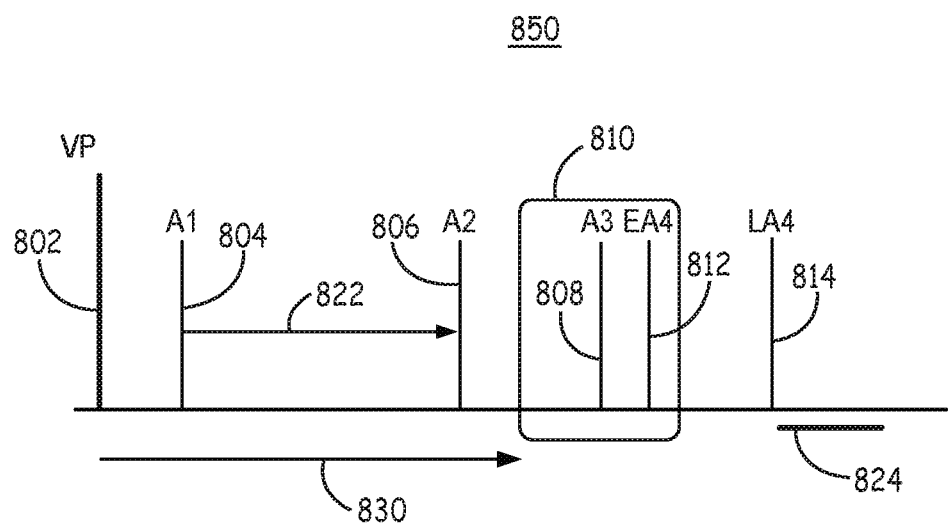
FIG. 11B is a timing diagram illustrating an alternative method for distinguishing between early and late atrial systolic events detected from a motion sensor signal for controlling ventricular pacing.

FIG. 11B is a timing diagram 850 illustrating an alternative method for discriminating between early and late A4 events for use in confirming A4 event detections and controlling ventricular pacing. In some examples, the time interval to an A3 event may be determined, e.g., from the averaged motion sensor signal as shown in FIG. 7. The A4 refractory period 830 may be set to expire prior to an expected time of the A3 event 808 (but later than the expected time of the A2 event 806). In some examples, the A4 refractory period 830 may initially be set to expire after the expected time of the A3 event but may be adjusted shorter than an expected A3 event time in response to a decreasing trend of the A2 event time interval, e.g., as described in conjunction with FIGS. 8 and 10.

When the A4 refractory period 830 expires earlier than an expected A3 event time, an A3 event window 810 may be used to distinguish an early A4 event 812 from a late A4 event 814. For example, if an A4 event detection 812 occurs after expiration of an A4 refractory period 830, but before expiration of an A3 window 810, the A4 event 812 is confirmed as an early A4 event based on an analysis of the A2 event time interval 822 before starting an AV pacing interval in response to the early A4 event 812. If the A2 event time interval 822 is determined to be shortened compared to one or more preceding A2 event time interval(s) or other A2 event time shortening criteria, the early A4 event 812 is confirmed as an A4 event. Otherwise the early A4 event 812 is ignored for the purposes of setting an AV pacing interval. The LR pacing interval (not explicitly shown in FIG. 11B) that is started upon VP 802 is allowed to continue running.

If a late A4 event 814 is detected after the expiration of the A3 window 810, confirmation of the late A4 event 814 based on the A2 event time interval 822 may not be required. An AV pacing interval 824 may be set immediately in response to the late A4 event detection.

Various examples of a intracardiac ventricular pacemaker configured to deliver atrial-synchronized ventricular pacing have been described according to illustrative embodiments. The intracardiac ventricular pacemaker is configured to detect A4 events from a motion sensor signal for controlling the atrial-synchronized ventricular pacing according to various methods described above. The methods described herein and represented by the accompanying flow charts and timing diagrams may combined or modified to include steps performed in a different order or combination than the illustrative examples shown. Furthermore, other circuitry may be conceived by one of ordinary skill in the art for implementing the techniques disclosed herein; the particular examples described herein are illustrative in nature and not intended to be limiting. It is appreciated that various modifications to the referenced examples may be made without departing from the scope of the disclosure and the following claims.

The invention claimed is:

1. An intracardiac ventricular pacemaker, comprising:
a pulse generator configured to generate and deliver pacing pulses to a ventricle of a patient's heart via electrodes coupled to the pacemaker;
a motion sensor configured to produce a motion signal comprising an atrial systolic event and at least one ventricular diastolic event; and
a control circuit coupled to the motion sensor and the pulse generator and configured to:
set an atrial refractory period;
determine a ventricular diastolic event metric from the motion signal;
compare the ventricular diastolic event metric to change criteria to detect a change in the ventricular diastolic event metric compared to at least one previously determined ventricular diastolic event metric;
adjust the atrial refractory period in response to detecting the change;
detect the atrial systolic event from the motion signal;
set an atrioventricular pacing interval in response to detecting the atrial systolic event after an expiration of the atrial refractory period; and
control the pulse generator to deliver a pacing pulse to a ventricle of the patient's heart in response to the atrioventricular pacing interval expiring.

2. The pacemaker of claim 1, wherein:
the motion sensor signal comprises a first ventricular diastolic event occurring with ventricular relaxation of a patient's heart and a second ventricular diastolic event occurring with passive ventricular filling;
the control circuit is configured to determine the ventricular diastolic event metric from at least one of the first ventricular diastolic event and the second ventricular diastolic event.

3. The pacemaker of claim 1, wherein the control circuit is configured to detect the change in the ventricular diastolic event metric by:
updating an average ventricular diastolic event metric using the ventricular diastolic event metric and at least one previously determined ventricular diastolic event metric; and
determining if the updated average ventricular diastolic event metric meets the change criteria.

4. The pacemaker of claim 2, wherein the control circuit is configured to set the atrial refractory period based on an expected time of the second ventricular diastolic event.

5. The pacemaker of claim 2, wherein the control circuit is configured to determine the ventricular diastolic event metric as a first ventricular diastolic event time interval from a preceding ventricular systolic event to the first ventricular diastolic event.

6. The pacemaker of claim 1, wherein the control circuit is further configured to: identify a ventricular electrical event;
start a ventricular lower rate pacing interval in response to identifying the ventricular electrical event; and
adjust the ventricular lower rate pacing interval in response to detecting the change in the ventricular diastolic event metric.

7. The pacemaker of claim 1, wherein the control circuit is configured to:
determine if the detected atrial systolic event is an early atrial systolic event in a ventricular cycle by comparing a time of detection of the atrial systolic event to early detection criteria;
determine if the ventricular diastolic event metric has decreased compared to a previously determined ventricular diastolic event metric in response to determining that the detected atrial systolic event is an early atrial systolic event;
confirm the early atrial systolic event in response to the ventricular diastolic event metric being decreased; and
set the atrioventricular pacing interval in response to confirming the early atrial systolic event.

8. The pacemaker of claim 7, wherein the control circuit is further configured to: responsive to determining the ventricular diastolic metric is not decreased, withhold setting the atrioventricular pacing interval in response to detecting the early atrial systolic event.

9. The pacemaker of claim 8, wherein the control circuit is further configured to:
detect a late atrial systolic event in the ventricular cycle in response to the motion signal crossing an atrial systolic event detection threshold amplitude after withholding the setting of the atrioventricular pacing interval; and
set the atrioventricular pacing interval in response to detecting the late atrial systolic event.

10. The pacemaker of claim 7, wherein the control circuit is further configured to: determine that the detected atrial systolic event is an early atrial systolic event in response to the motion signal crossing an atrial systolic event detection threshold amplitude during the atrial refractory period.

11. The pacemaker of claim 7, wherein:
the motion sensor signal comprises a first ventricular diastolic event occurring with ventricular relaxation of a patient's heart and a second ventricular diastolic event occurring with passive ventricular filling;
the control circuit is further configured to:
establish an expected time window of the second ventricular diastolic event; and
determine that the detected atrial systolic event is an early atrial systolic event in response to the motion signal crossing an atrial systolic event detection threshold amplitude during the expected time window of the second ventricular diastolic event.

12. The pacemaker of claim 11, wherein the control circuit is configured to:
determine an averaged motion signal;
detect the second ventricular diastolic event from the averaged motion signal;
establish the expected time window based on the second ventricular diastolic event detected from the averaged motion signal; and
set the atrial refractory period to expire based on a time of the second ventricular diastolic event in the averaged motion signal.

13. The pacemaker of claim 2, wherein the control circuit is configured to determine the ventricular diastolic event metric by determining a time interval from the second ventricular diastolic event to the atrial systolic event.

14. The pacemaker of claim 1, further comprising a housing enclosing the pulse generator, the motion sensor, and the control circuit, wherein the electrodes are housing-based electrodes.

15. A method performed by an intracardiac ventricular pacemaker having a motion sensor, comprising:
producing by the motion sensor a motion signal comprising an atrial systolic event and at least one ventricular diastolic event;
setting by a control circuit of the pacemaker an atrial refractory period;
determining by the control circuit a ventricular diastolic event metric from the motion signal;
comparing the ventricular diastolic event metric to change criteria to detect a change in the ventricular diastolic event metric compared to at least one previously determined ventricular diastolic event metric;
adjusting the atrial refractory period in response to detecting the change;
detecting the atrial systolic event from the motion signal;
setting an atrioventricular pacing interval in response to detecting the atrial systolic event after an expiration of the atrial refractory period; and
delivering a pacing pulse to a ventricle of the patient's heart via electrodes coupled to the pacemaker in response to the atrioventricular pacing interval expiring.

16. The method of claim 15, wherein the motion sensor signal comprises a first ventricular diastolic event occurring with ventricular relaxation of a patient's heart and a second ventricular diastolic event occurring with passive ventricular filling;
the method further comprising determining the ventricular diastolic event metric from at least one of the first ventricular diastolic event and the second ventricular diastolic event.

17. The method of claim 15, wherein detecting the change in the ventricular diastolic event metric comprises:
updating an average first ventricular diastolic event metric using the ventricular diastolic event metric and at least one previously determined ventricular diastolic event metric;
determining if the updated average ventricular diastolic event metric meets the change criteria.

18. The method of claim 16, further comprising setting the atrial refractory period based on an expected time of the second ventricular diastolic event.

19. The method of claim 16, further comprising determining the ventricular diastolic event metric as a first ventricular diastolic event time interval from a preceding ventricular systolic event to the first ventricular diastolic event.

20. The method of claim 15, further comprising:
identifying a ventricular electrical event;
starting a ventricular lower rate pacing interval in response to identifying the ventricular electrical event; and
adjusting the ventricular lower rate pacing interval in response to detecting the change in the ventricular diastolic event metric.

21. The method of claim 15, further comprising:
determining if the detected atrial systolic event is an early atrial systolic event in a ventricular cycle by comparing a time of detection to early detection criteria;
determining if the ventricular diastolic event metric has decreased compared to a previously determined ventricular diastolic event metric in response to determining that the detected atrial systolic event is an early atrial systolic event;
confirming the early atrial systolic event in response to the ventricular diastolic event metric being decreased; and
setting the atrioventricular pacing interval in response to confirming the early atrial systolic event.

22. The method of claim 21, further comprising:
responsive to the ventricular diastolic event metric not being decreased, withholding setting the atrioventricular pacing interval in response to detecting the early atrial systolic event.

23. The method of claim 22, further comprising:
detecting a late atrial systolic event in the ventricular cycle in response to the motion signal crossing an atrial systolic event detection threshold amplitude after withholding the setting of the atrioventricular pacing interval; and
setting the atrioventricular pacing interval in response to detecting the late atrial systolic event.

24. The method of claim 21, further comprising:
determining that the detected atrial systolic event is an early atrial systolic event in response to the motion signal crossing an atrial systolic event detection threshold amplitude during the atrial refractory period.

25. The method of claim 21, wherein:
the motion sensor signal comprises a first ventricular diastolic event occurring with ventricular relaxation of a patient's heart and a second ventricular diastolic event occurring with passive ventricular filling;
the method further comprising:
establishing an expected time window of the second ventricular diastolic event; and
determining that the detected atrial systolic event is an early atrial systolic event in response to the motion signal crossing an atrial systolic event detection threshold amplitude during the expected time window of the second ventricular diastolic event.

26. The method of claim 25, further comprising:
determining an averaged motion signal;
detecting the second ventricular diastolic event from the averaged motion signal;
establishing the expected time window based on the second ventricular diastolic event detected from the averaged motion signal; and
setting the atrial refractory period to expire based on a time of the second ventricular diastolic event in the averaged motion signal.

27. The method of claim 16, wherein determining the ventricular diastolic event metric comprises determining a time interval from the second ventricular diastolic event to the atrial systolic event.

28. The method of claim 15, further comprising delivering the pacing pulse via housing-based electrodes carried by a housing enclosing the pulse generator, the motion sensor, and the control circuit.

29. A non-transitory computer-readable medium storing a set of instructions which when executed by a control circuit of an intracardiac ventricular pacemaker having a motion sensor, cause the pacemaker to:
produce by the motion sensor a motion signal comprising an atrial systolic event and at least one ventricular diastolic event;
set an atrial refractory period;
determine a ventricular diastolic event metric;

compare the ventricular diastolic event metric to change criteria to detect a change in the ventricular diastolic event metric compared to at least one previously determined ventricular diastolic event metric;
adjust the atrial refractory period in response to detecting the change;
detect the atrial systolic event from the motion signal;
set an atrioventricular pacing interval in response to detecting the atrial systolic event after an expiration of the atrial refractory period; and
deliver a pacing pulse to a ventricle of the patient's heart via electrodes coupled to the pacemaker in response to the atrioventricular pacing interval expiring.

* * * * *